(12) United States Patent
Prestidge et al.

(10) Patent No.: US 6,626,868 B1
(45) Date of Patent: Sep. 30, 2003

(54) NEEDLE APPARATUS

(76) Inventors: Dean B. Prestidge, 7 Key West Drive, Mullaloo, Western Australia 6027 (AU); Maxwell E. Whisson, 5/70 Subiaco Road, Subiaco, Western Australia 6008 (AU)

( * ) Notice: Subject to any disclaimer, the term of this patent is extended or adjusted under 35 U.S.C. 154(b) by 0 days.

(21) Appl. No.: 09/806,385

(22) PCT Filed: Sep. 29, 1999

(86) PCT No.: PCT/AU99/00827

§ 371 (c)(1),
(2), (4) Date: Mar. 29, 2001

(87) PCT Pub. No.: WO00/20058

PCT Pub. Date: Apr. 13, 2000

(30) Foreign Application Priority Data

Oct. 14, 1998 (AU) .............................................. PP 6477
Oct. 6, 1998 (AU) .............................................. PP 6347
Jan. 22, 1999 (AU) .............................................. PP 8318

(51) Int. Cl.$^7$ ............................................. A61M 5/178
(52) U.S. Cl. .................. 604/158; 604/159; 604/164.12; 604/165.01
(58) Field of Search .................................. 604/158, 159, 604/161, 164.01, 164.06, 164.08, 164.12, 165.01, 165.03, 168.01

(56) References Cited

U.S. PATENT DOCUMENTS

| | | | | |
|---|---|---|---|---|
| 5,205,829 A | * | 4/1993 | Lituchy | 604/164 |
| 5,665,072 A | * | 9/1997 | Yoon | 604/164.12 |
| 5,676,156 A | * | 10/1997 | Yoon | 600/564 |
| 5,752,936 A | * | 5/1998 | Chen | 600/576 |
| 6,186,960 B1 | * | 2/2001 | Tripp et al. | 600/576 |

* cited by examiner

Primary Examiner—Edward K. Look
Assistant Examiner—John K Fristoe, Jr.
(74) Attorney, Agent, or Firm—Bachman & LaPointe, P.C.

(57) ABSTRACT

A needle apparatus has a thin walled catheter enclosing a tubular needle having a sharp point, the catheter and the needle being relatively moveable longitudinally a short distance, from a first position where the needle projects from the catheter and to a second position at which the sharp point is located within the catheter. The needle remains in the fluid pathway of the needle apparatus at all times. The needle apparatus is arranged to pierce tissue when the catheter and the needle are in the first position.

21 Claims, 24 Drawing Sheets

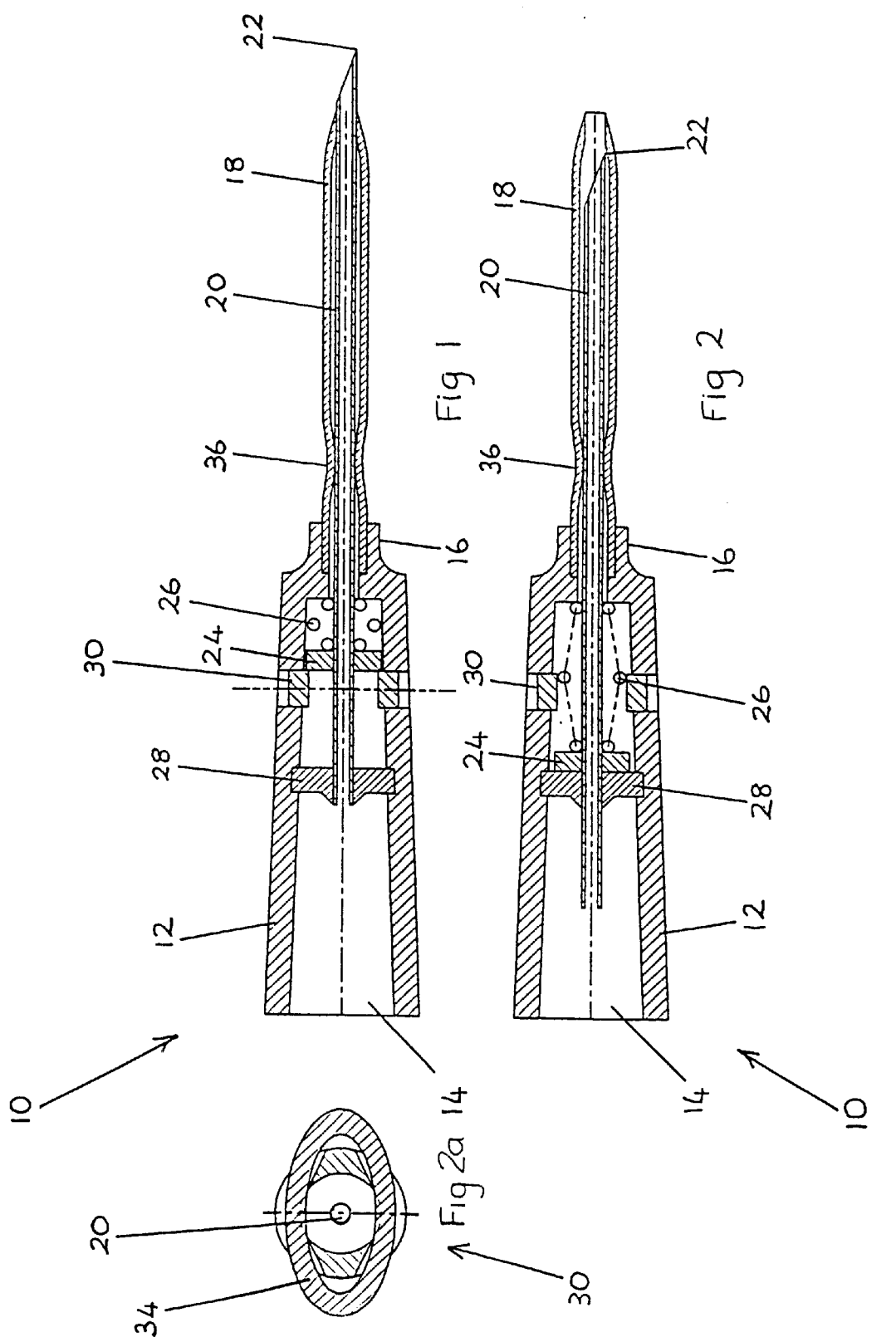

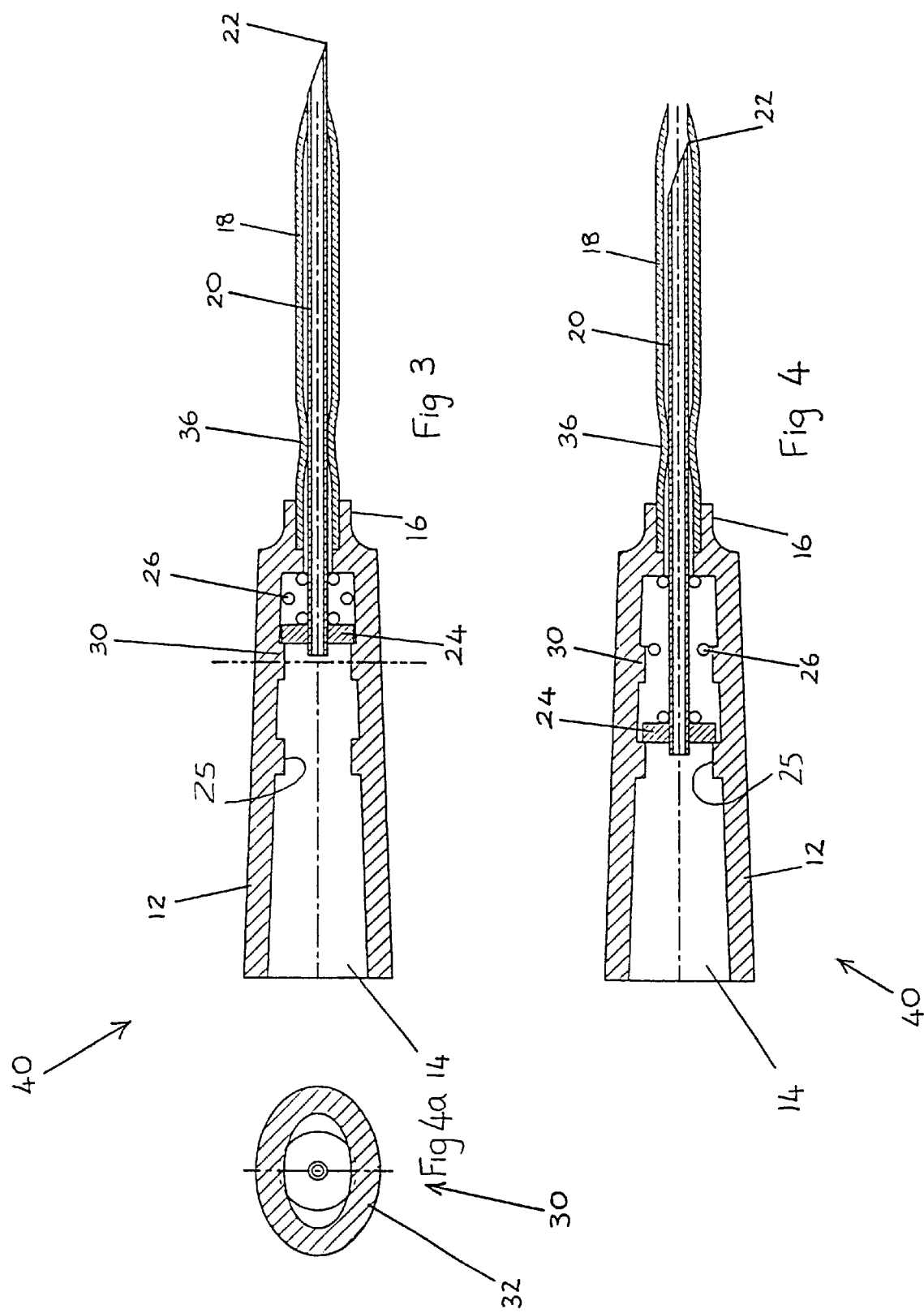

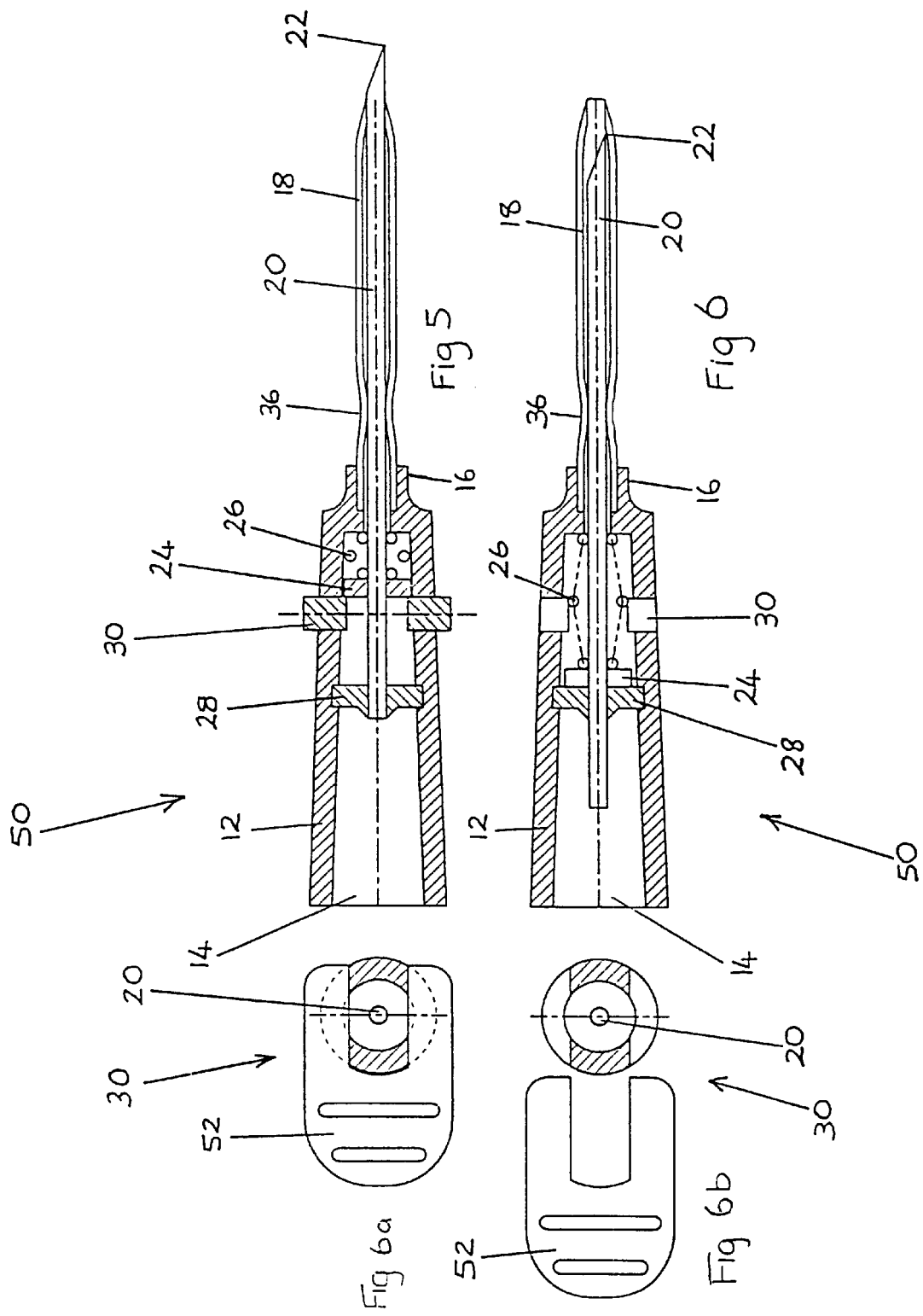

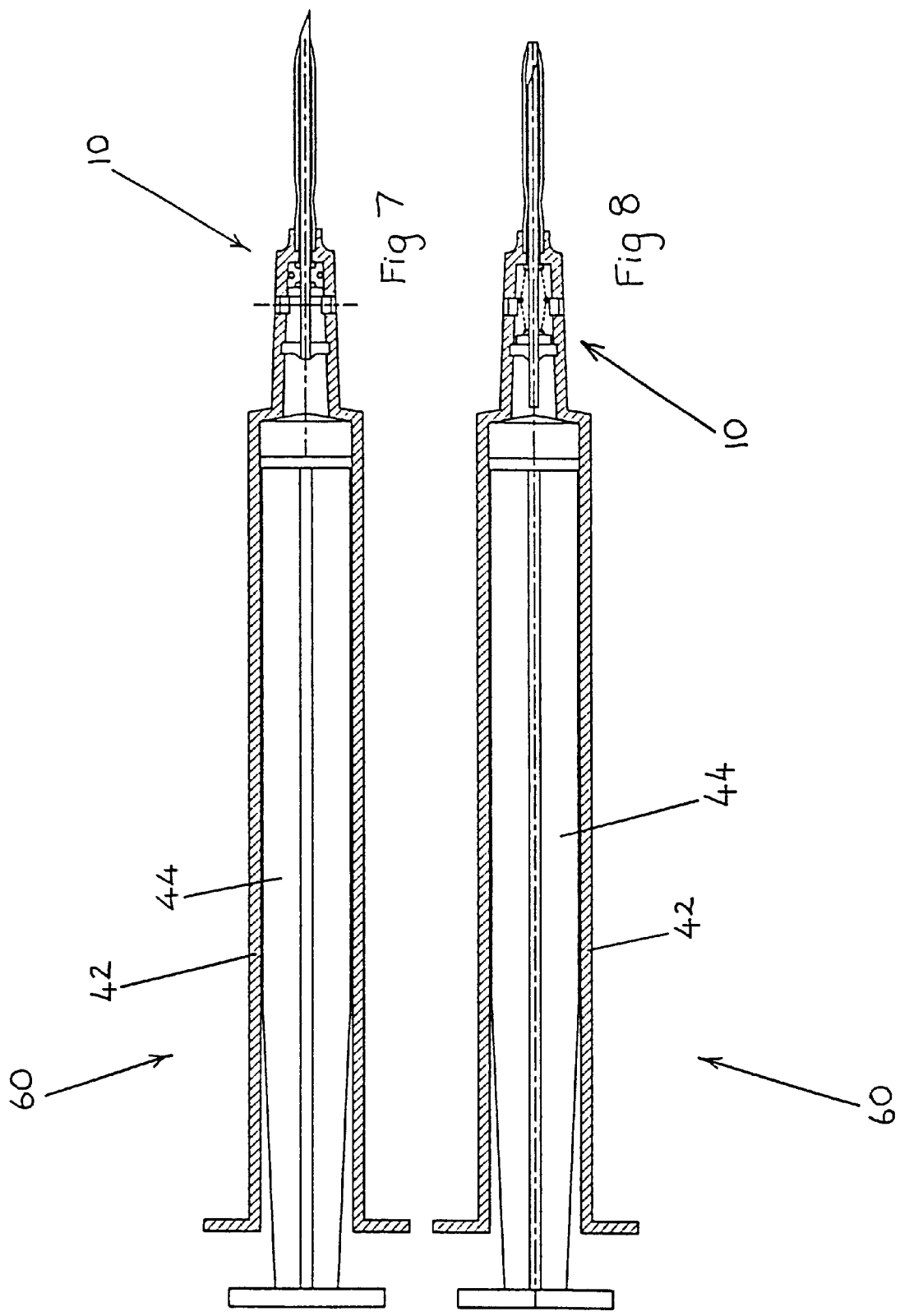

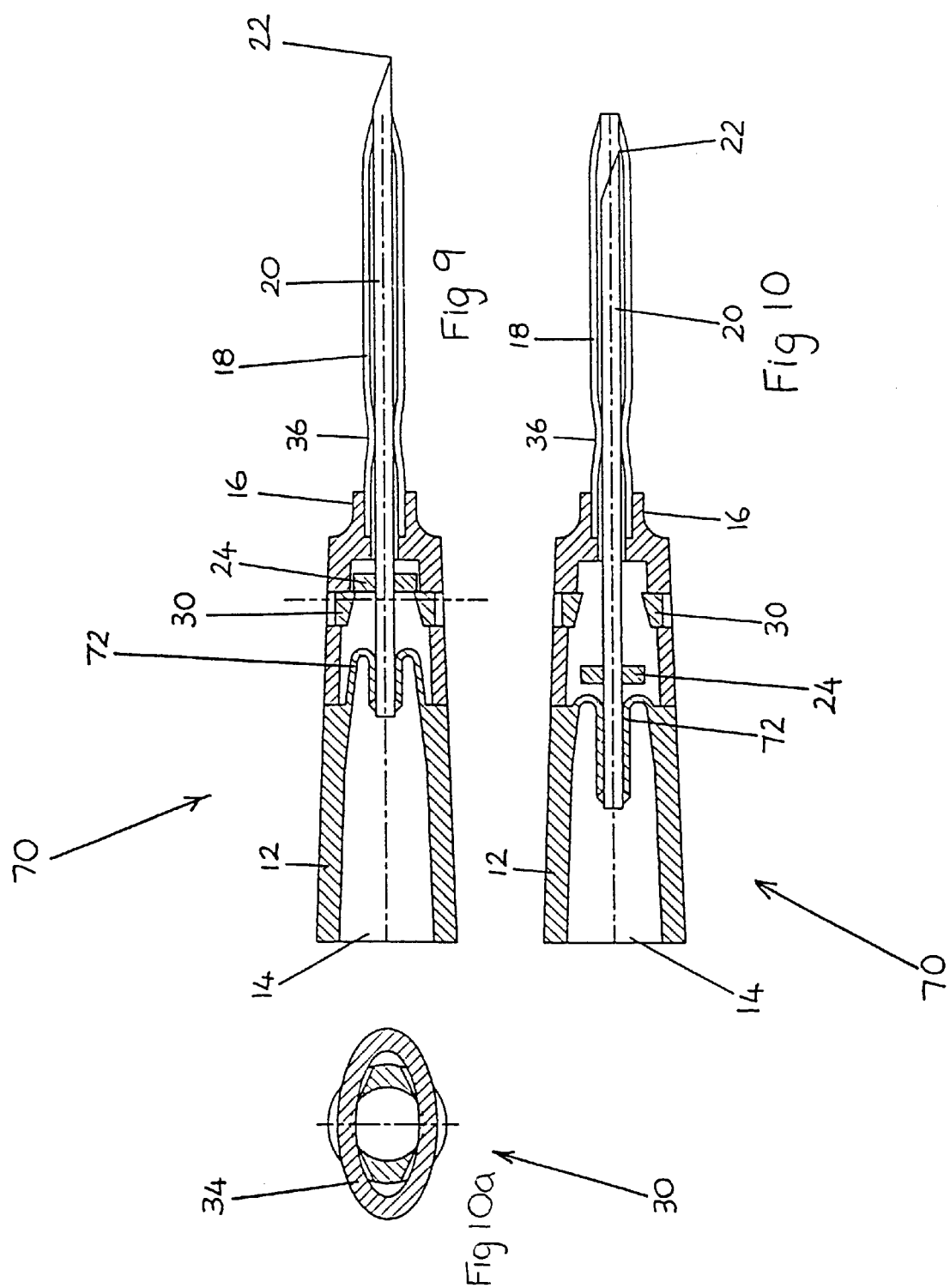

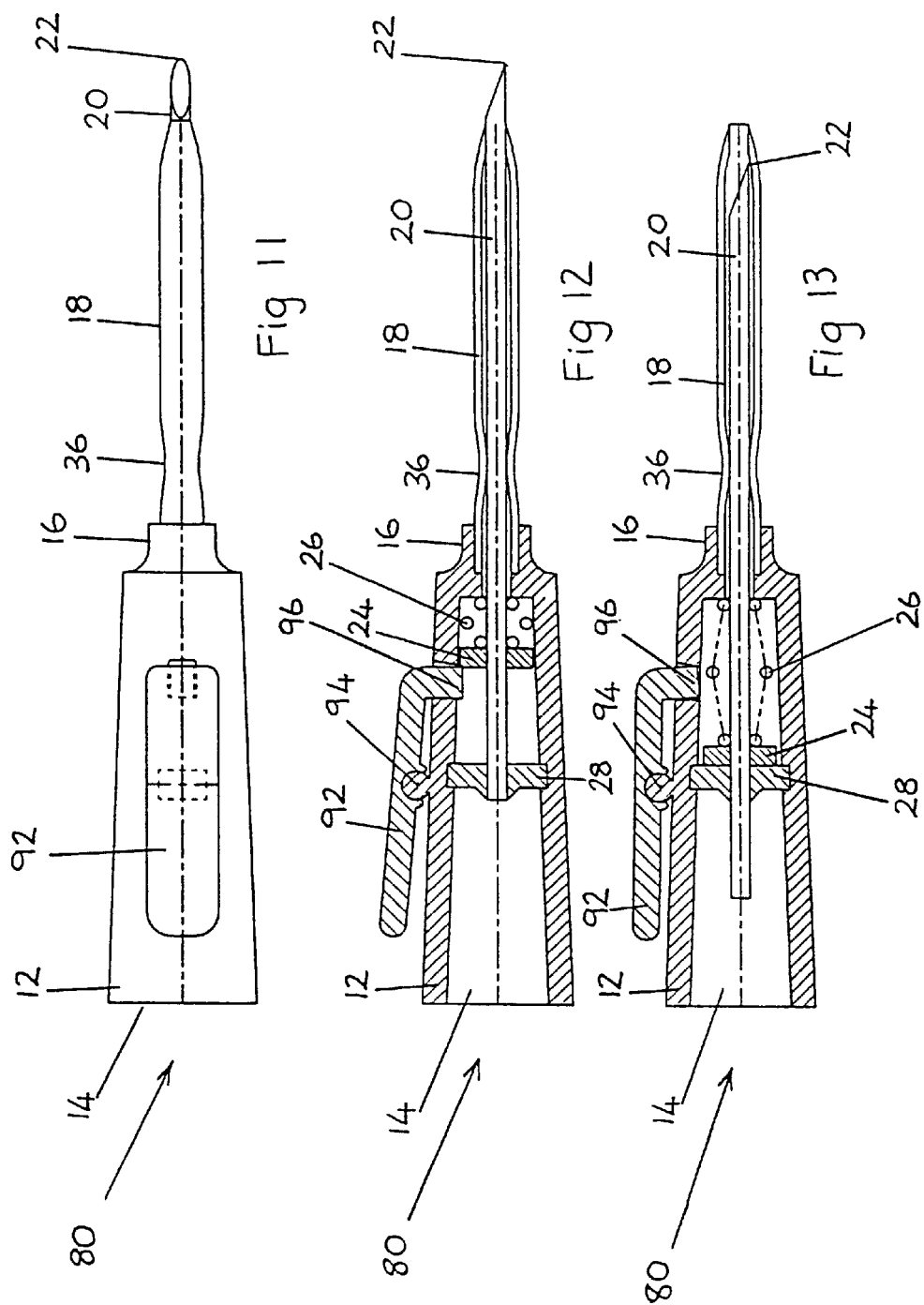

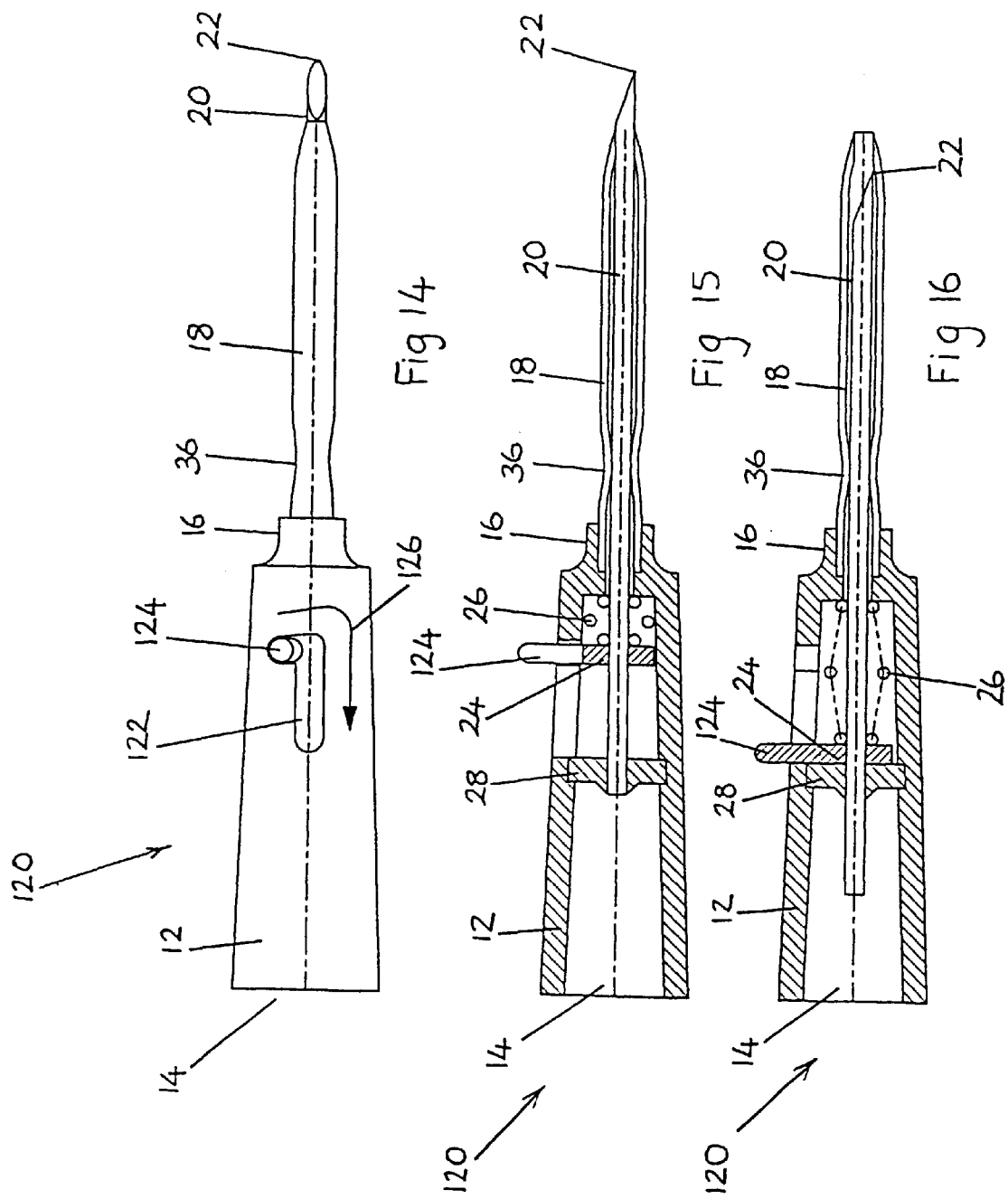

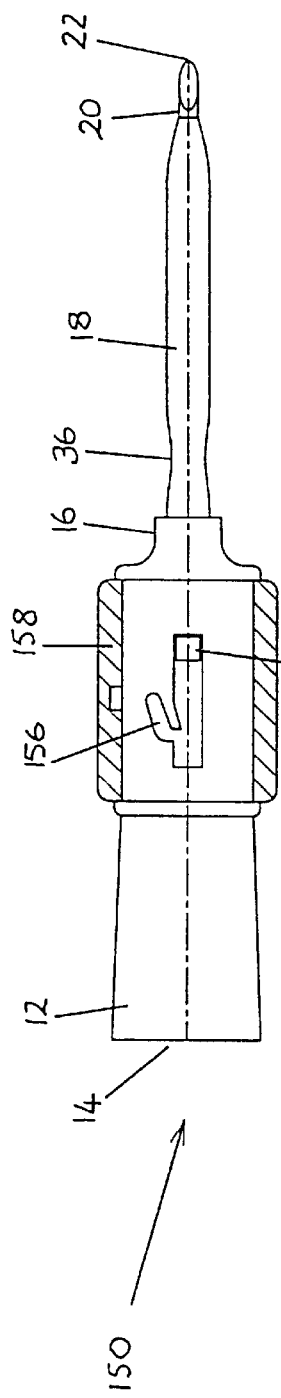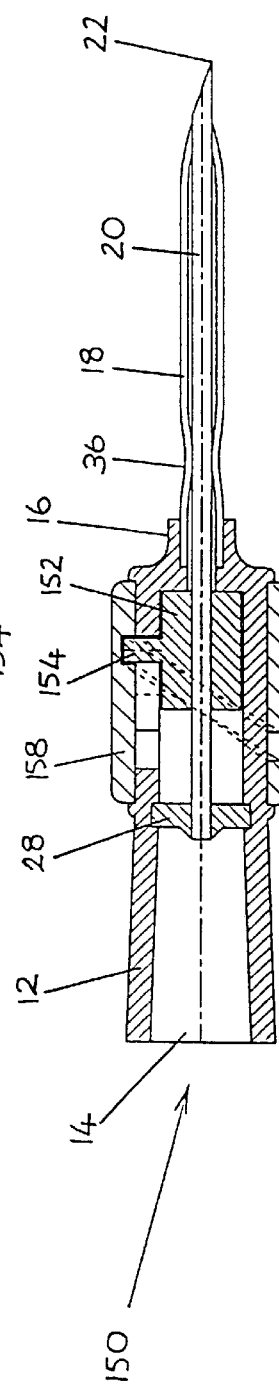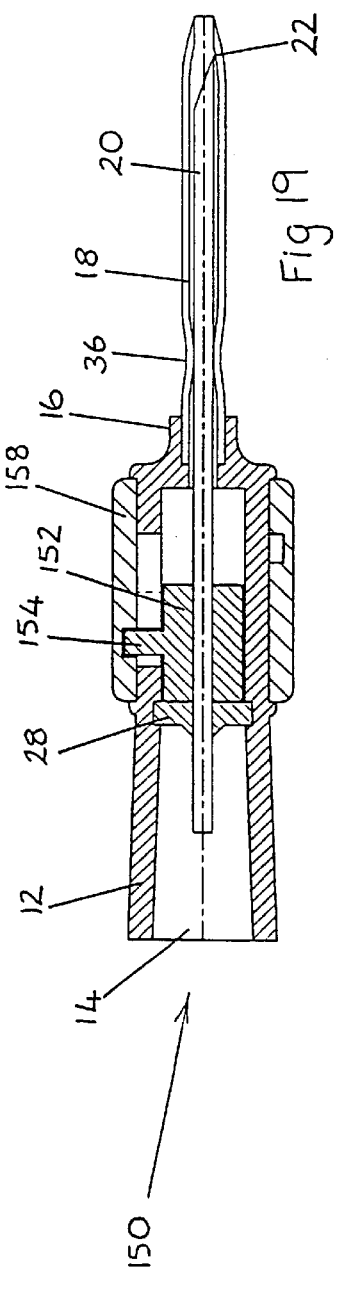

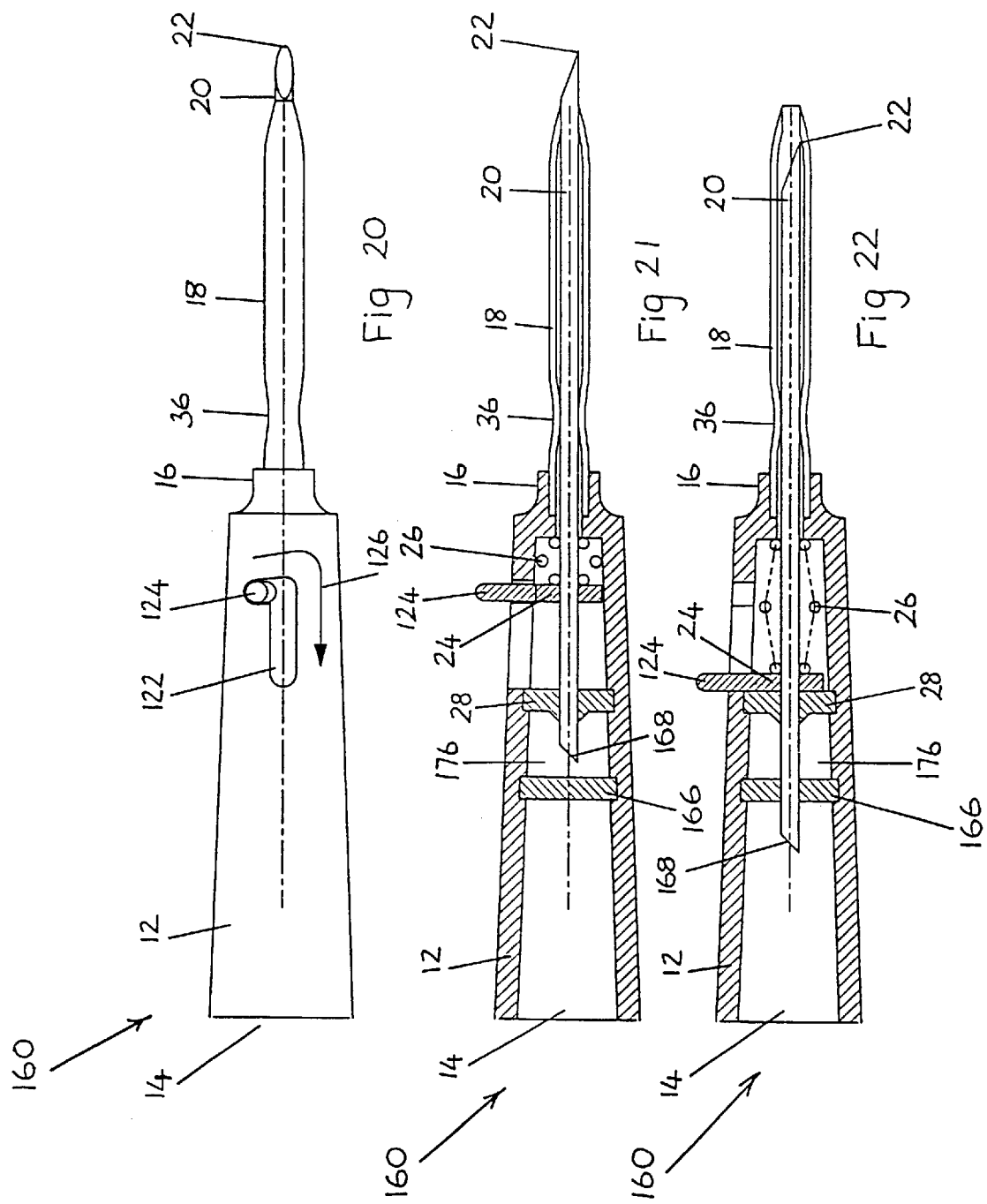

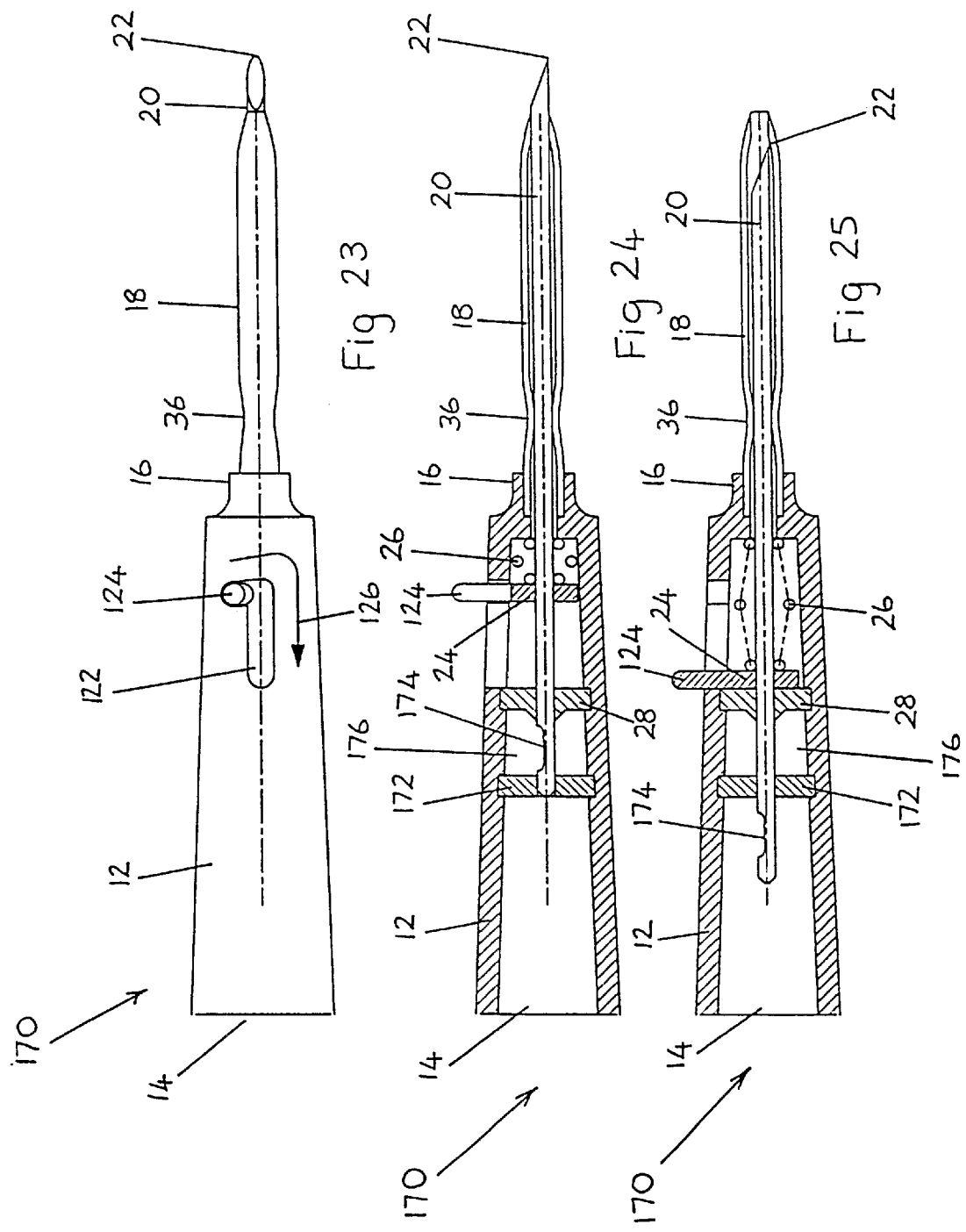

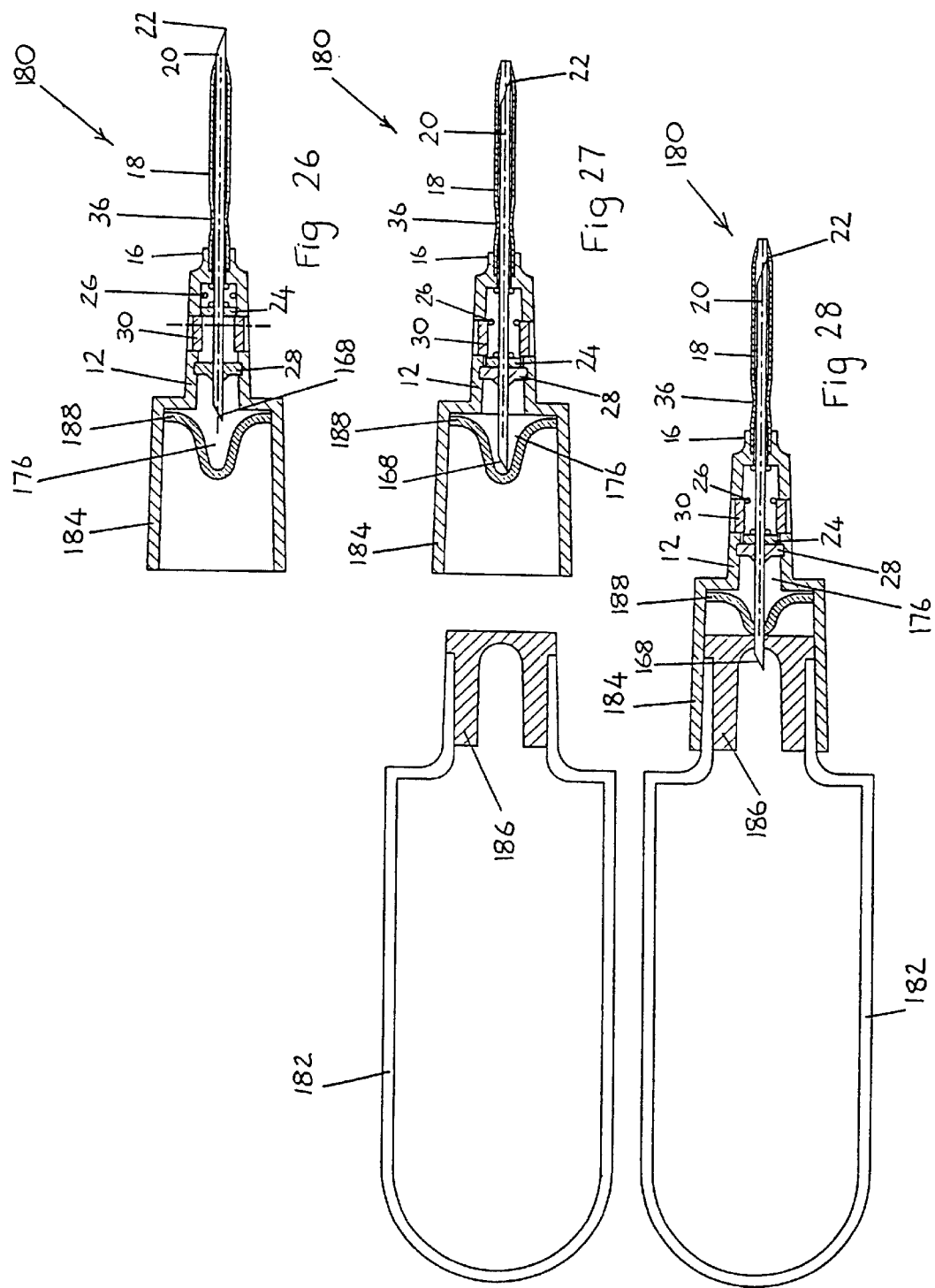

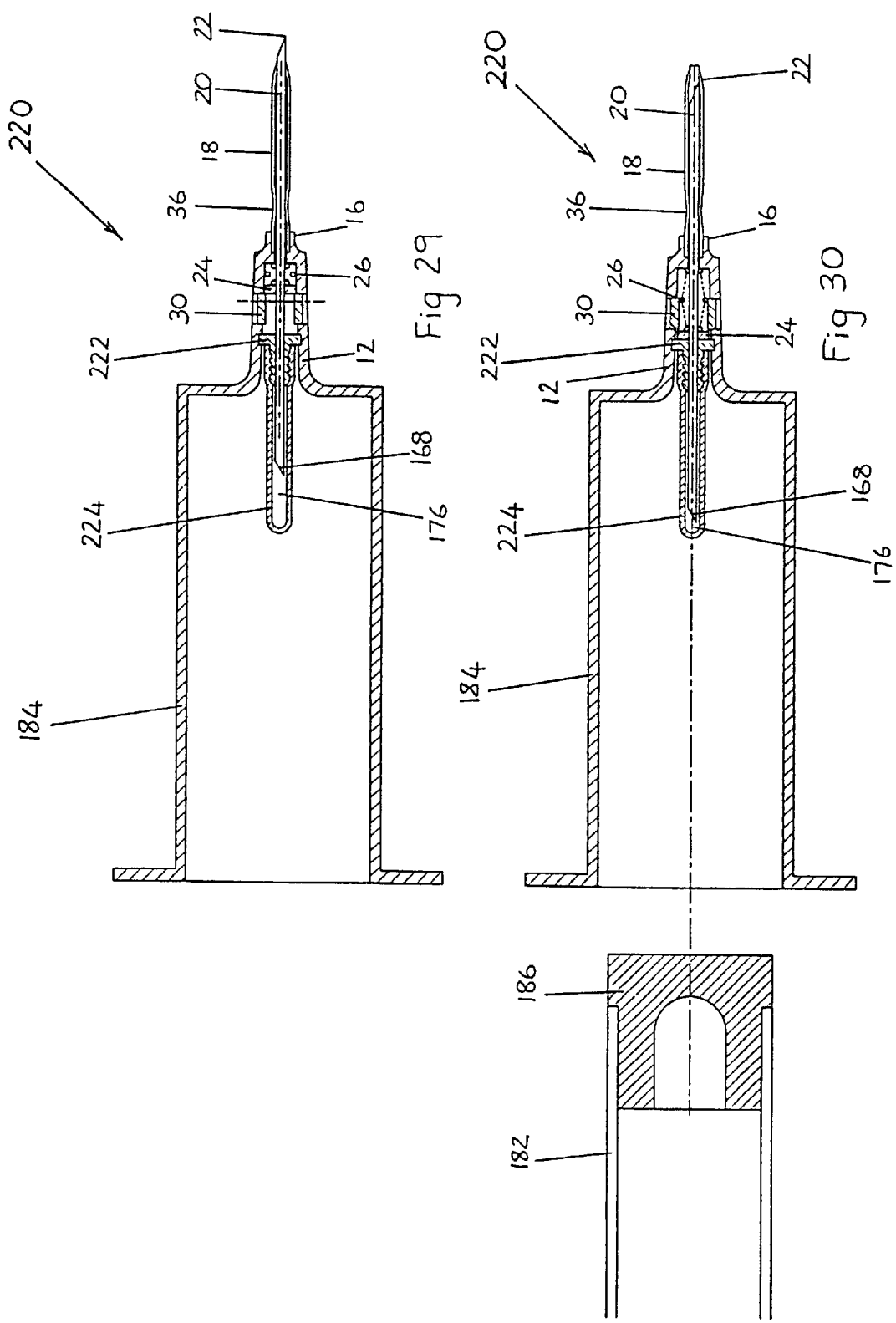

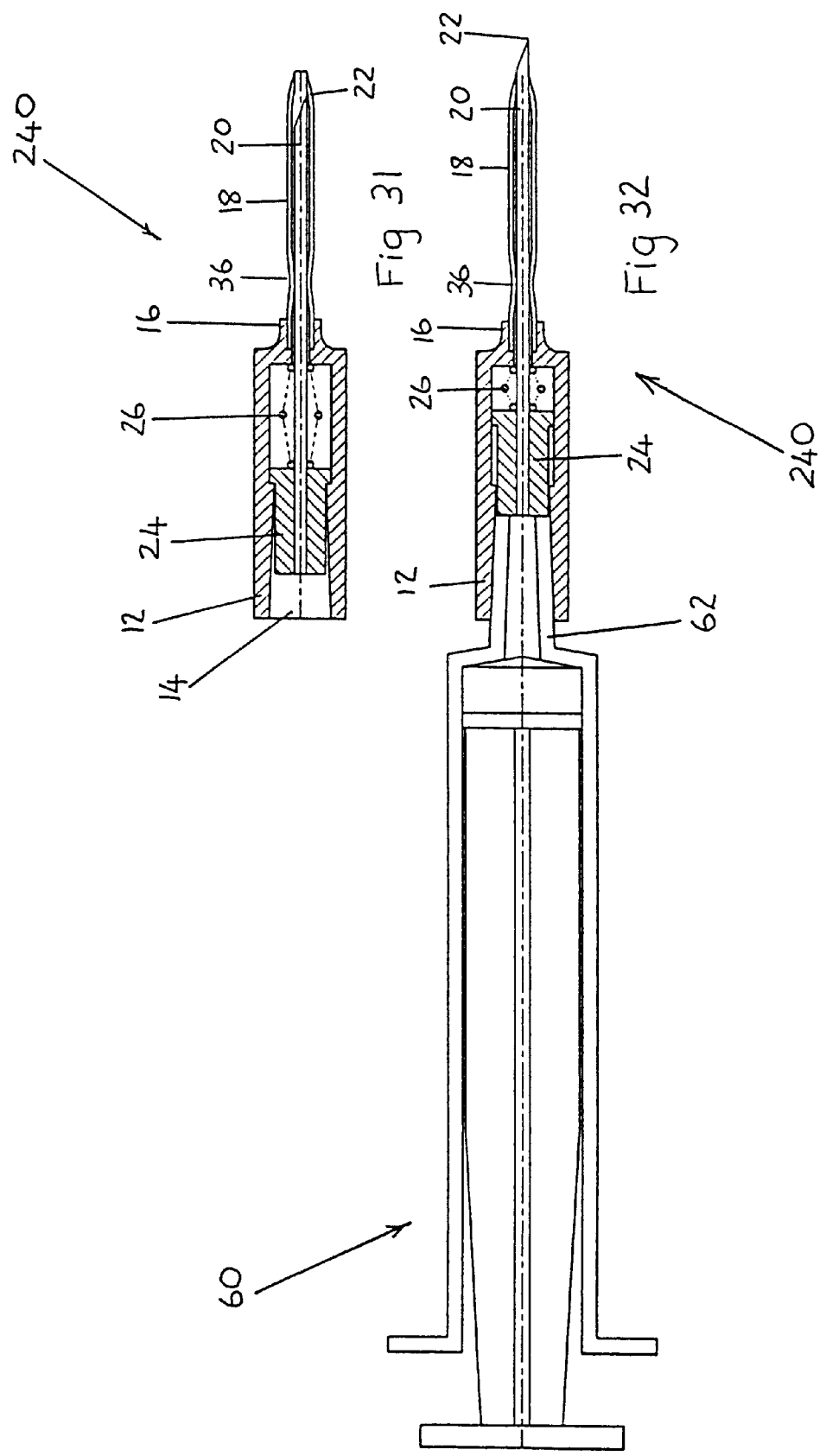

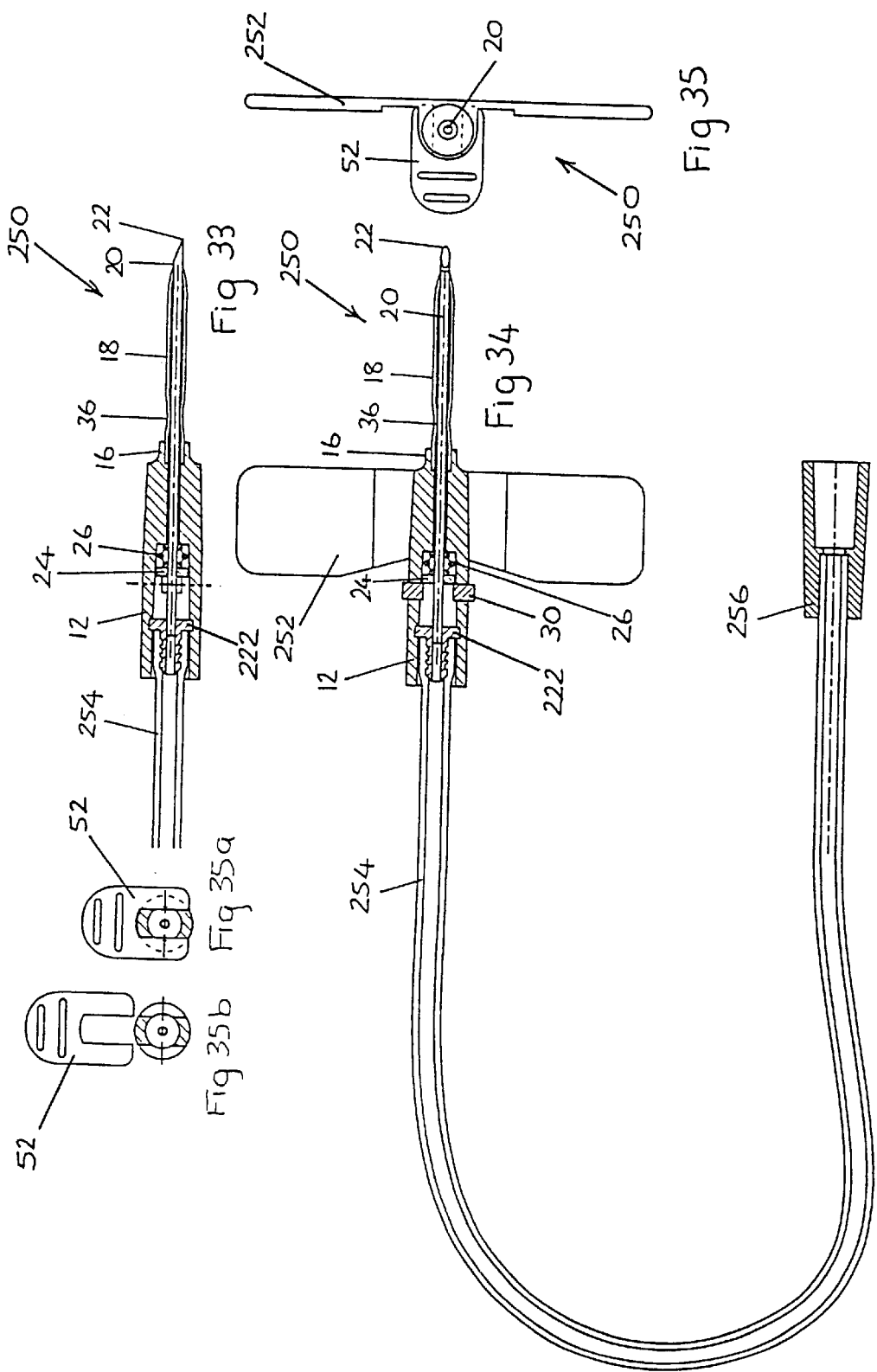

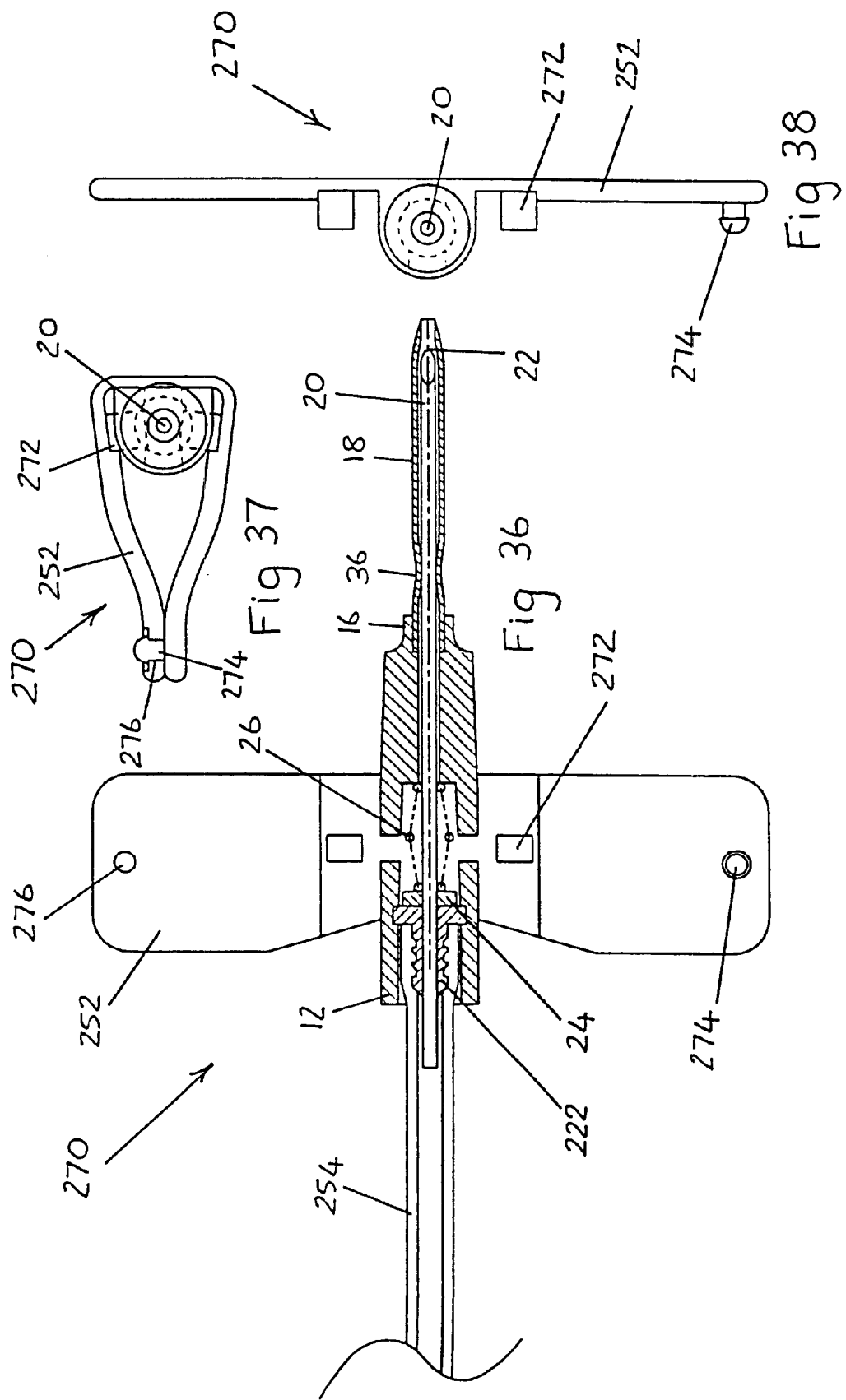

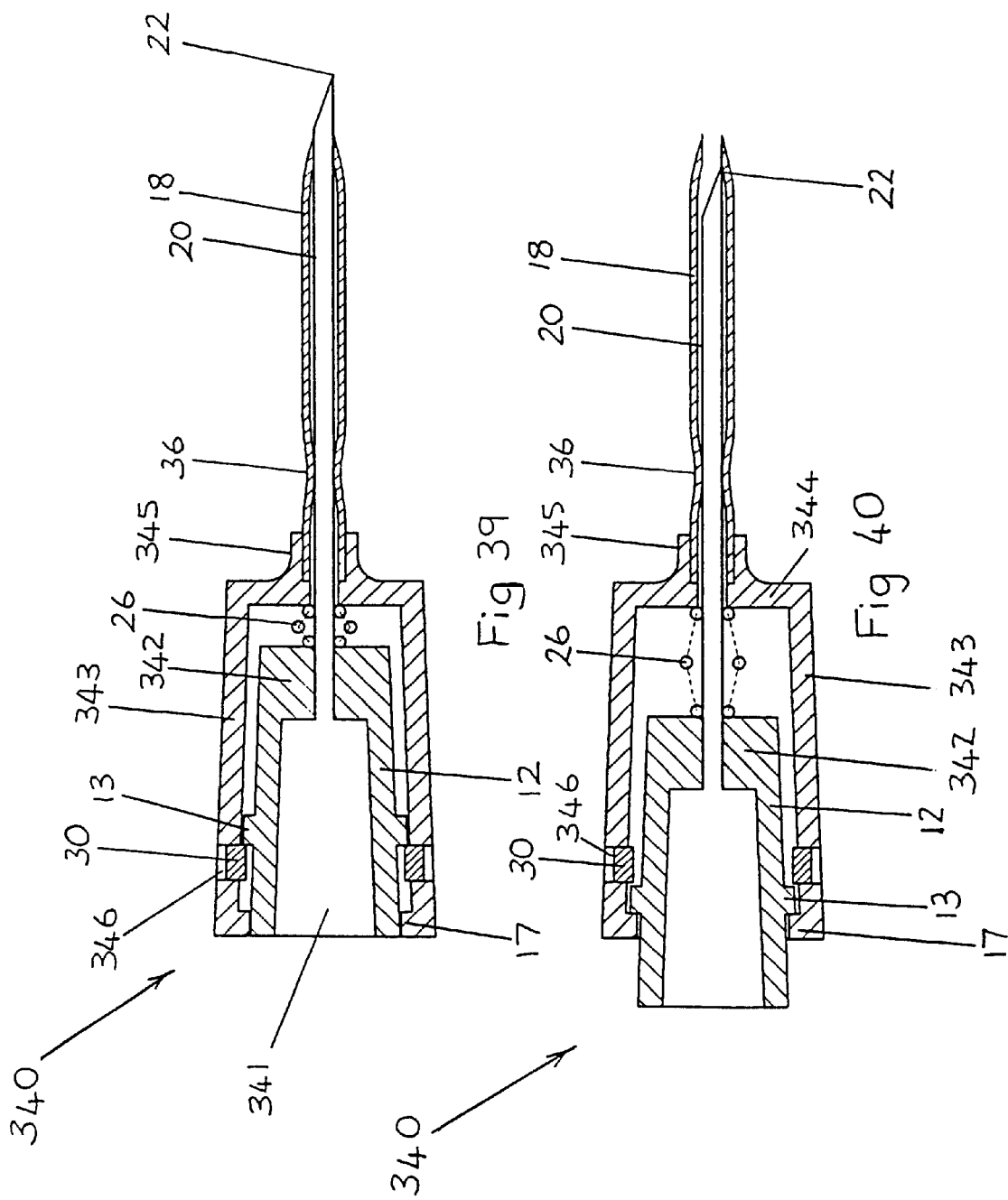

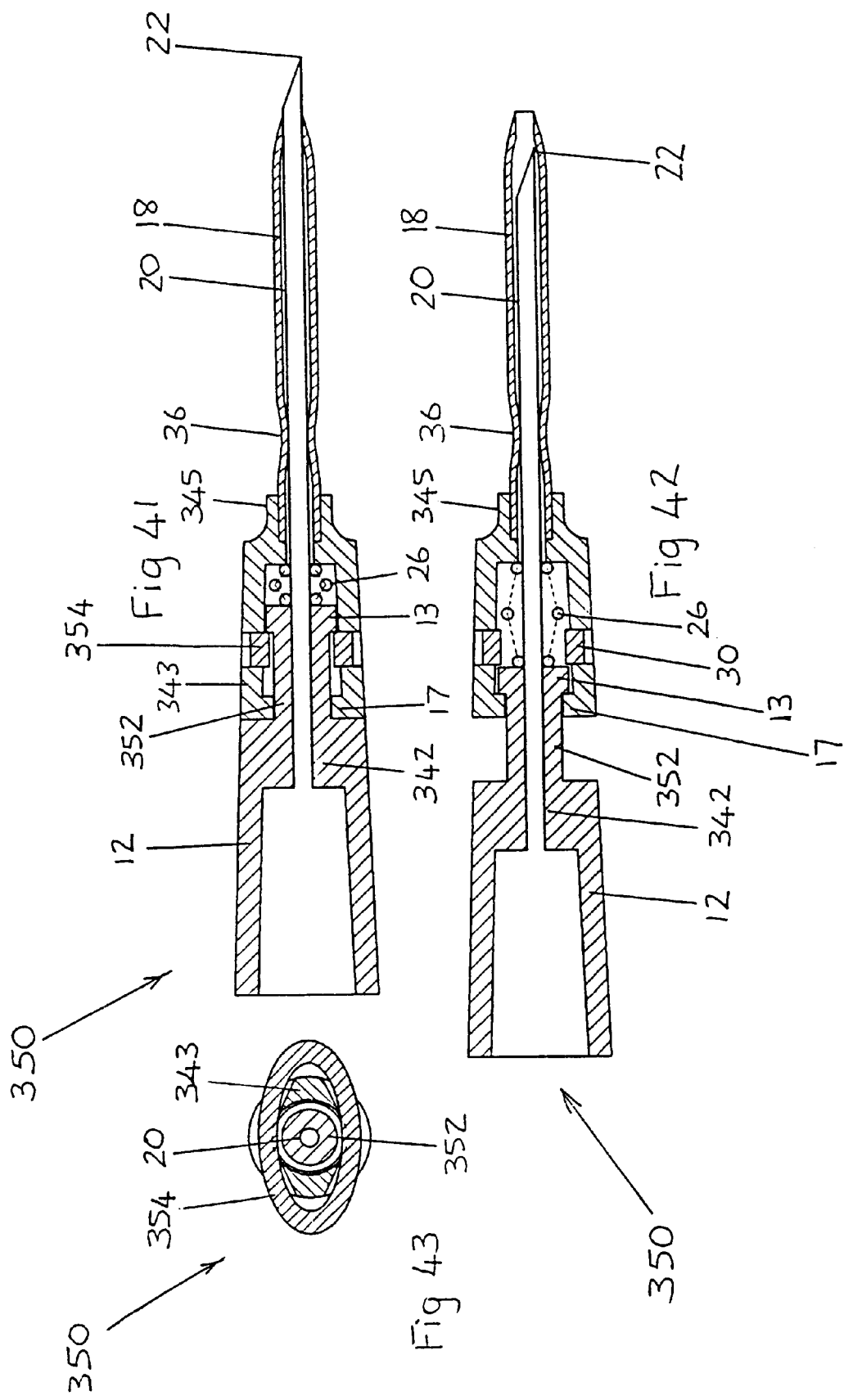

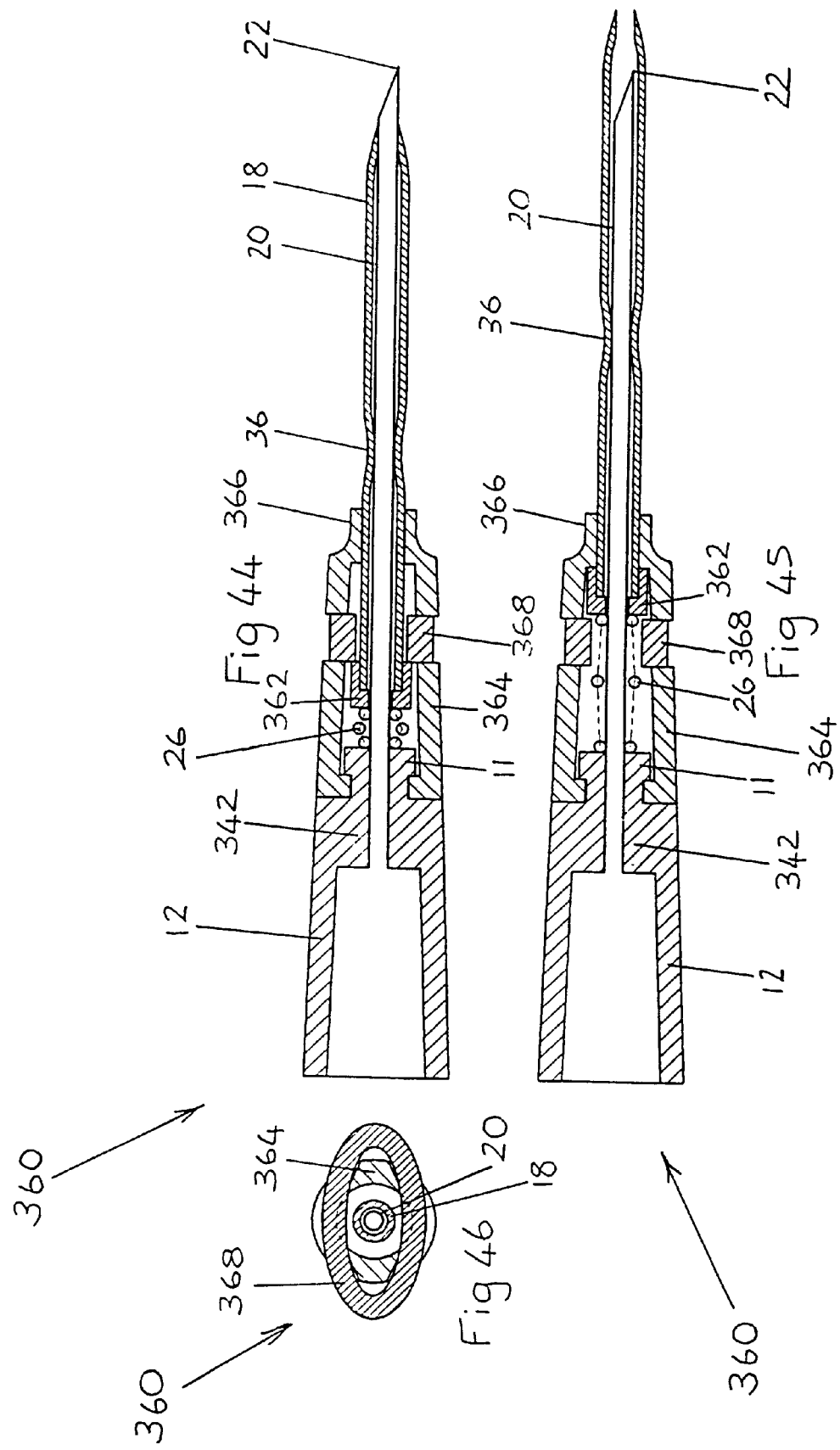

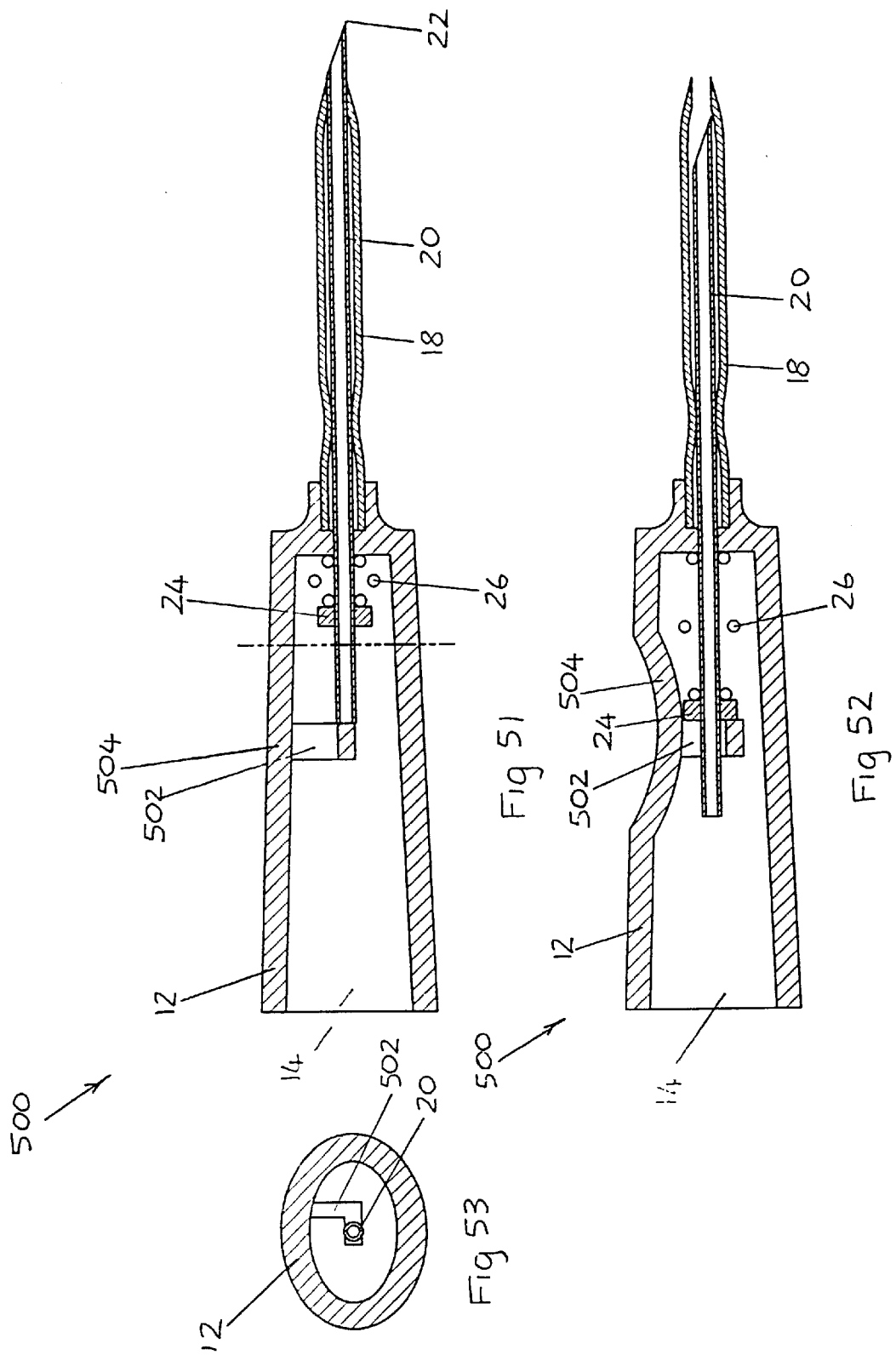

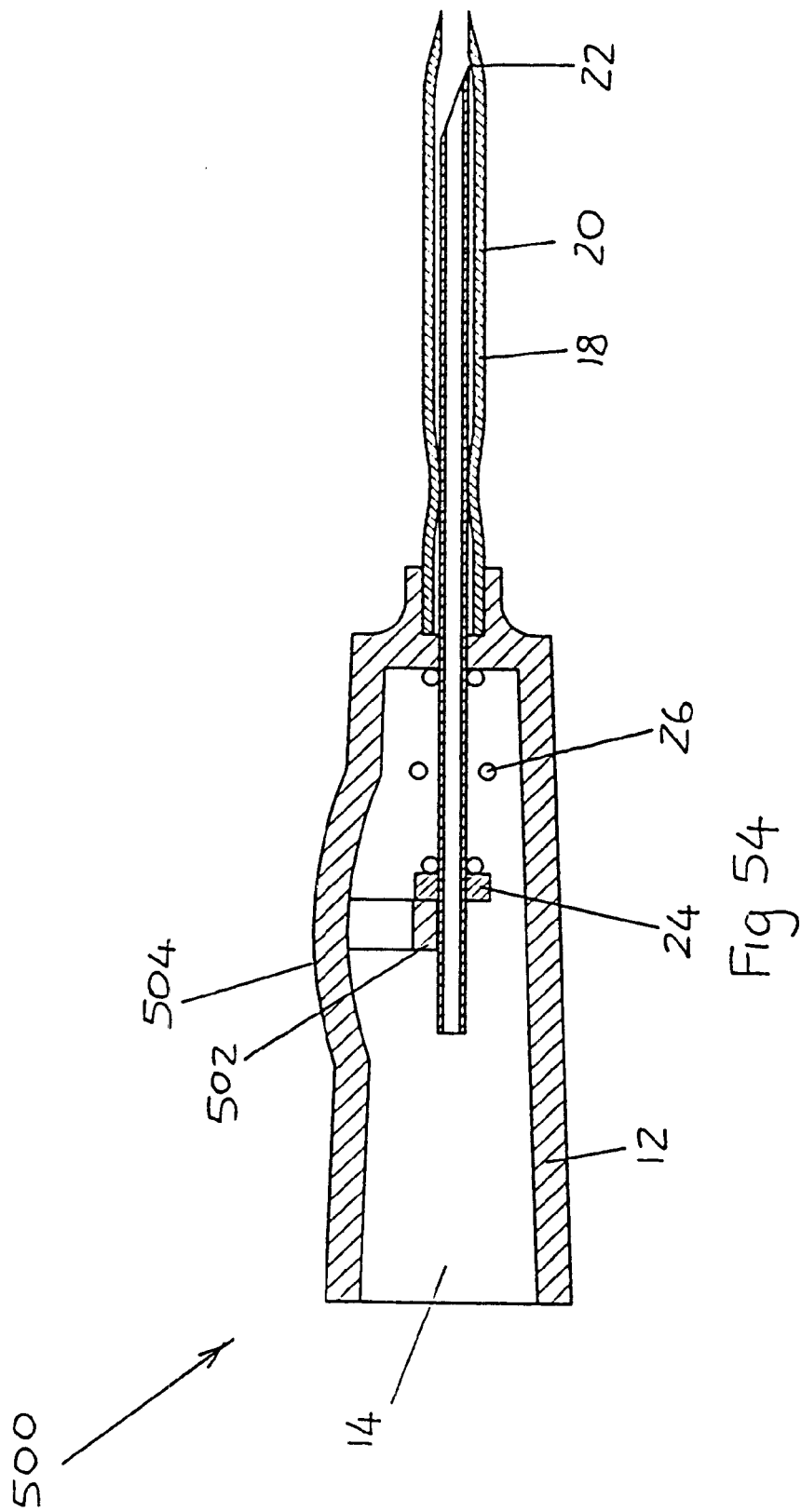

NEEDLE APPARATUS

FIELD OF THE INVENTION

The present invention relates to a needle apparatus.

PRIOR ART

Injection devices which use a sharp needle to enter human tissue are now widely recognized as being hazardous to users and other individuals because the sharp point, contaminated by its exposure to the tissue of the first person may penetrate the skin of a second person and in doing so may carry micro-organisms from the patient on whom the injection device was first used into the tissue of a second person. Such transmission may result in the development of disease in the second person. When the penetration of the skin is accidental it is referred to as "needlestick injury" or "needleprick injury".

Disease transmission by this means is now recognised as a major cause of occupational disease transmission to healthcare workers. The prevention of such transmission has resulted in the setting up of expensive and inefficient procedures and has caused an increase in the cost of providing medical support.

Transmission of disease may also result from the deliberate re-use of a sharp need by a second person and this is a major cause of transmission of such diseases as hepatitis C and AIDS (HIV) amongst users of narcotic intravenous drugs. Many other infectious diseases may be transmitted from one person to another by contaminated needles.

Three main strategies have been put in place to reduce the risk of disease transmission by contaminated needles. These are (i) strict adherence to methods and procedures which reduce the risk of accidental needlestick injury, (ii) the widespread distribution of secure containers (sharps containers) into which the used needles can be placed as soon as possible after use, and (iii) the invention and development of injection devices whereby the sharp needle point can be covered soon after use, so reducing the risk of needlestick injury, and in many examples, reducing the possibility of the injection device being used a second time.

A disadvantage of all of these strategies is that they all cause some perturbation of optimal or most efficient clinical practice and all incur increased expense in providing medical care. Often these factors mean that the safety measures fail not because the device does not provide safety but simply because they are not put into universal practice. Most importantly, these strategies and techniques may leave a "window of risk" in the interval between removing the contaminated needle from the tissue of a person and putting into effect the chosen procedure or technique to make the contaminated needle safe.

The prior art shows a great variety of methods of rendering sharp used needles safe. The prior art can be satisfactorily classified into three types which are:

(i) sheaths, in which a cover slides forward toward and over the needle and the sharp needle point after use, (ii) needle retraction devices in which the needle is pulled back into the whole injection device—such as a syringe—until the sharp tip is enclosed and safe, this movement requiring novel and often expensive alternative fluid paths formed by sliding seals, side holes, or re-curved double—pointed needles, and (iii) needle capture devices which are similar to needle retraction but involve a detachable needle assembly linking a needle base with a syringe and a catch linking an inner part of the syringe, usually the piston or plunger, with the detachable needle assembly, so operating only after the syringe is used and emptied.

Most of these strategies can only be applied after removal of the contaminated sharp needle from the tissue of the patient and a risk of needlestick injury remains until they are applied.

It is an object of the present invention to provide a needle apparatus which can be used in much the same way as conventional tubular injection needles without requiring difficult or complex techniques to maintain fluid transfer passages during movement of the needle within the apparatus.

BRIEF DESCRIPTION OF THE INVENTION

In accordance with one aspect of the present invention there is provided a needle apparatus comprising a thin walled catheter having a free end closely enclosing a tubular needle having a sharp point, characterised in that the needle and/or the catheter is mounted to a housing and the needle and the catheter are longitudinally moveable relative to one another between a first position at which the needle extends from the catheter a short distance and a second position at which the sharp point is located within the catheter adjacent the free end thereof, the needle remaining in a fluid pathway of the needle apparatus at all times, means being provided for positively retaining the needle and the catheter in the first position, the means for positively retaining the needle and the catheter in the first position including a manually operable catch member which upon release enables the needle and the catheter to move relatively to the second position, means being provided for moving the needle relative to the catheter to the second position upon release of the catch member, and the needle apparatus being arranged to pierce tissue when the catheter and the needle are in the first position.

In accordance with a further aspect of the present invention there is provided a needle apparatus comprising a thin walled catheter having a free end closely enclosing a tubular needle having a sharp point, characterised in that the needle and the catheter are longitudinally moveable relative to one another between a first position at which the needle extends from the catheter a short distance and a second position at which the sharp point is located within the catheter adjacent the free end thereof, the needle remaining in the fluid pathway of the needle apparatus at all times, means being provided for positively retaining the needle and the catheter in the first position including a catch member which upon release enables the needle and the catheter to move to the second position, the needle apparatus being arranged to pierce tissue when the catheter and the needle are in the first position, wherein the needle has a rearward end containing an aperture and having a further sharp point arranged to pierce a barrier member in the housing when the catheter and the needle move to the second position so as to establish fluid communication with a chamber which contains or is arranged to contain fluid.

In accordance with a yet further aspect of the present invention there is provided a needle apparatus comprising a thin walled catheter having a free end closely enclosing a tubular needle having a sharp point, characterised in that the needle and the catheter are longitudinally moveable relative to one another between a first position at which the needle extends from the catheter a short distance and a second position at which the sharp point is located within the catheter adjacent the free end thereof, the needle remaining in the fluid pathway of the needle apparatus at all times, means being provided for positively retaining the needle and the catheter in the first position including a catch member which upon release enables the needle and the catheter to move to the second position, the needle apparatus being arranged to pierce tissue when the catheter and the needle are in the first position, means being provided for positively retaining the needle and the catheter in the first position wherein the apparatus includes a housing having a flexible wall portion which upon a change in internal pressure of the housing moves laterally to act as the catch member to enable the catheter and the needle to move to the second position.

BRIEF DESCRIPTION OF THE DRAWINGS

The present invention will now be described, by way of example, with reference to the accompanying drawings, in which:

FIG. 1 is a cross-sectional view of a first embodiment of a needle apparatus in accordance with the present invention in a first extended position ready for use to pierce body tissue and transfer fluid to or from the tissue;

FIG. 2 is a view similar to FIG. 1 in which the needle apparatus is in a second retracted position suitable for transferring fluid to or from the living body or for safe disposal after use;

FIG. 2a is a schematic plan view of a catch member of the needle apparatus of FIGS. 1 and 2;

FIG. 3 is a cross-sectional view of a second embodiment of the needle apparatus in accordance with the present invention in an extended position;

FIG. 4 is a view similar to FIG. 3 in which the needle apparatus is in a retracted position;

FIG. 4a is a schematic plan view of a catch member of the needle apparatus of FIGS. 3 and 4;

FIG. 5 is a cross-sectional view of a third embodiment of the needle apparatus in accordance with the present invention in an extended position;

FIG. 6 is a view similar to FIG. 5 in which the needle apparatus is in a retracted position;

FIG. 6a is a schematic plan view of a catch member of the needle apparatus of FIGS. 5 and 6 in an extended condition;

FIG. 6b is a schematic plan view of the catch member of FIG. 6a in a retracted condition;

FIG. 7 is a cross-sectional view of a fourth embodiment of the needle apparatus in accordance with the present invention in an extended position fixed on a conventional syringe ready for insertion into tissue to perform an injection;

FIG. 8 is a view similar to FIG. 3 in which the needle apparatus is in a retracted position suitable for transferring fluid to or from the living body or for safe disposal after use;

FIG. 9 is a cross-section view of a fifth embodiment of the needle apparatus in accordance with the present invention in an extended position;

FIG. 10 is a cross-sectional view similar to FIG. 9 in which the needle apparatus is in an retracted position;

FIG. 10a is a schematic plan view of a catch member of the needle apparatus of FIG. 9 and 10;

FIG. 11 is a plan view of a sixth embodiment of the needle apparatus in accordance with the present invention in an extended position;

FIG. 12 is a cross-sectional view of the sixth embodiment of the needle apparatus in accordance with the present invention in an extended position;

FIG. 13 is a view similar to FIG. 12 in which the needle apparatus of FIGS. 11 and 12 is shown in a retracted position;

FIG. 14 is a plan view of a seventh embodiment of the needle apparatus in accordance with the present invention in an extended position;

FIG. 15 is a cross-sectional view of the seventh embodiment of the needle apparatus in accordance with the present invention in an extended position;

FIG. 16 is a view similar to FIG. 15 in which the needle apparatus of FIGS. 14 and 15 is shown in a retracted position;

FIG. 17 is a plan view of an eighth embodiment of the needle apparatus in accordance with the present invention in an extended position;

FIG. 18 is a cross-sectional view of the eighth embodiment of the needle apparatus in accordance with the present invention in an extended position;

FIG. 19 is a view similar to FIG. 18 in which the needle apparatus of FIGS. 17 and 18 is shown in a retracted position;

FIG. 20 is a plan view of a ninth embodiment of the needle apparatus in accordance with the present invention in an extended position;

FIG. 21 is a cross-sectional view of the ninth embodiment of the needle apparatus in accordance with the present invention in an extended position;

FIG. 22 is a view similar to FIG. 21 in which the apparatus of FIGS. 20 and 21 is shown in a retracted position;

FIG. 23 is a plan view of a tenth embodiment of the needle apparatus in accordance with the present invention in an extended position;

FIG. 24 is a cross-sectional view of the tenth embodiment of the needle apparatus in accordance with the present invention in an extended position;

FIG. 25 is a view similar to FIG. 24 in which the needle apparatus of FIGS. 23 and 24 is shown in a retracted position;

FIG. 26 is a cross-sectional view of an eleventh embodiment of the needle apparatus in accordance with the present invention in an extended position;

FIG. 27 is a view similar to FIG. 26 in which the needle apparatus of FIG. 26 is shown in a retracted position together with a cross-sectional view of a vacuum sampling vial which may be fitted to the needle apparatus;

FIG. 28 is a view similar to FIG. 27 in which the needle apparatus of FIGS. 26 and 27 is shown in a retracted position together with a cross-sectional view of a vacuum sampling vial which is shown fitted to the needle apparatus ready to collect blood flowing through the needle apparatus from a blood vessel;

FIG. 29 is a cross-sectional view of a twelfth embodiment of the needle apparatus in accordance with the present invention shown in an extended position;

FIG. 30 is a view similar to FIG. 29 in which the needle apparatus of FIG. 29 is shown in a retracted position together with a cross-sectional view of part of a vacuum sampling vial ready to be fitted to the needle apparatus for the purpose of collecting blood flowing through the needle apparatus;

FIG. 31 is a cross-sectional view of a thirteenth embodiment of the needle apparatus in accordance with the present invention in a retracted position;

FIG. 32 is a view similar to FIG. 31 in which the needle apparatus of FIG. 31 is in an extended position together with a syringe connected by a Luer fitting to the needle apparatus ready to commence an injection;

FIG. 33 is a cross-sectional view of portion of a fourteenth embodiment of the needle apparatus in accordance with the present invention shown in an extended position;

FIG. 34 is a view similar to FIG. 33 in which the needle apparatus is in an extended position and includes a flexible tubular line suitable for connection to standard intravenous equipment for collecting blood or delivering medication into a blood vessel;

FIG. 35 is an end elevation of the needle apparatus shown in FIGS. 33 and 34;

FIG. 35a is a schematic plan view of a catch member of the apparatus of FIGS. 33 to 35 in an extended condition;

FIG. 35b is a schematic plan view of a catch member of the apparatus of FIGS. 33 to 35 in a retracted condition;

FIG. 36 is a cross-sectional view of a fifteenth embodiment of the needle apparatus in accordance with the present invention shown in a retracted position;

FIG. 37 is an end elevation of the embodiment shown in FIG. 36 with finger grips positioned to maintain the extended position; and FIG. 38 is an end elevation of the embodiment shown in FIG. 37 with finger grips positioned to cause the retracted position.

FIG. 39 is a longitudinal sectional view of a sixteenth embodiment of the needle apparatus in accordance with the present invention in first position ready for use to pierce body tissue and transfer fluid to or from the tissue;

FIG. 40 is a view similar to FIG. 39 in which the needle apparatus is in a second position suitable for the transfer of parenteral fluid into or from the living body and ready for safe disposal after use;

FIG. 41 is a schematic sectional view of the seventeenth embodiment of the needle apparatus in accordance with the present invention showing a preferred catch member, retaining the needle apparatus in a first position suitable for piercing the living tissue and for transferring parenteral fluid;

FIG. 42 is a view similar to FIG. 41 in which the needle apparatus is shown in a second position suitable for transferring parenteral fluid or for disposal after use;

FIG. 43 is a schematic cross-sectional view of a catch member of the apparatus of FIGS. 41 and 42, retaining the needle apparatus in a first or second position;

FIG. 44 is a longitudinal sectional view of a eighteenth embodiment of the needle apparatus in accordance with the present invention shown in a first position;

FIG. 45 is a view similar to FIG. 44 in which the needle apparatus is shown in a second position;

FIG. 46 is a schematic cross-sectional view of the eighteenth embodiment showing a catch member of the apparatus of FIGS. 44 and 45, retaining the needle apparatus in a first or second position;

FIG. 51 is a longitudinal sectional view of a twenty first embodiment of the present invention shown in a first position ready to enter a blood vessel of a patient;

FIG. 52 is a view similar to FIG. 51 showing the needle apparatus retracted due to decreased internal pressure;

FIG. 53 is a transverse sectional view of the apparatus of FIG. 51; and

FIG. 54 is a view similar to FIG. 52 showing the needle apparatus retracted due to increased internal pressure.

DESCRIPTION

Figure 47:
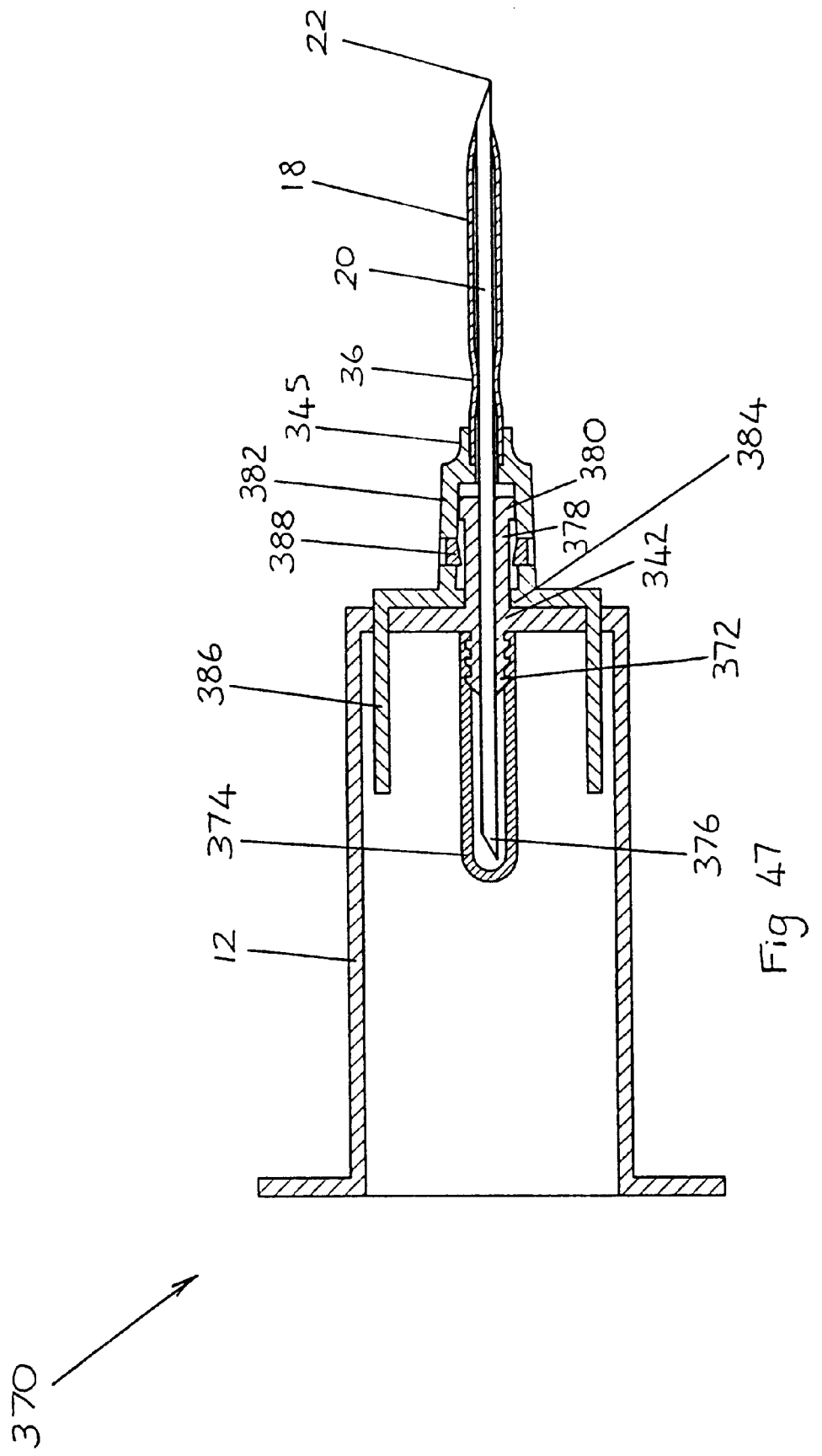
FIG. 47 is a longitudinal sectional view of a nineteenth embodiment of the needle needle apparatus in accordance with the present invention shown in a first position ready to enter a blood vessel of a patient and ready to receive a vacuum sampling tube.

The needle apparatus of the present invention will now be described in greater detail by reference to the Figures, in which the same numbers are used to refer to similar parts throughout.

In the descriptions which follow, "needle" means a thin walled stiff tube or C section such as a steel tube, sharpened at least at one end. "Catheter" means a thin walled flexible tube, attached at one end and free or capable of being made free at the other end and preferably formed of inert plastic elastomer which can be fitted closely but slidingly to the outer wall of the chosen needle. The mechanical properties of the needle and catheter may be optimised to suit particular applications and the hardness and stiffness may if desired be varied along the length.

In FIG. 1 and 2 of the drawings, there is shown a needle apparatus 10 including a Luer or similar housing 12 having an open end 14 able to receive amating Luer or similar fitting on a syringe or other injection device, and a closed end 16. A thin-walled catheter 18 is mounted in the end 16 of housing 12 and extends away from the end 16. A needle 20 is disposed within the catheter 18 and has a sharp point 22 extending a short distance from an outer end of the catheter 18. The needle 20 extends into the housing 12 through an aperture to form a low pressure sliding seal.

A flange 24 is mounted to the needle 20 such as by shrink fitting or by adhesive, internally of the housing 12. A spring 26, such as a coil spring, is mounted about the needle 20 within the housing 12 between the flange 24 and the end 16.

Further, a guide means 28 is provided within the housing 12 and forms a sliding low pressure seal with the needle 20. As shown in FIGS. 1 and 2 the needle 20 is engaged at all times with the guide means 28. Further, a catch member 30 is provided for retaining the flange 24 in the position shown in FIG. 1 at which the spring 26 is compressed. The catch member 30 includes a resilient elliptical member 34 shown in FIG. 2a, or alternatively a resilient portion of its wall, which is arranged to be compressed manually so as to release the catch member 30 by disengagement from the flange 24. This allows the needle 20 to be retracted under urging of the spring 26 until the flange 24 engages with the guide means 28. The retraction of the needle 20 causes the sharp point 22 to be withdrawn from the exposed position shown in FIG. 1 to a protected position within the catheter 28 as shown in FIG. 2. This does not disturb the fluid path through the needle 20 and through the outer end of the catheter 18. The point 22 is withdrawn in this movement a short distance inside the catheter 18 which is preferably chosen to be slightly more than the longitudinal compression of the catheter to be expected such as when dropping the needle apparatus 10 attached to a loaded syringe point first onto the skin of a person.

The distance through which point 22 is withdrawn within the catheter 18 is typically less than 15 mm and preferably less than 5 mm and more preferably less than 2 mm, depending on the length and chosen mechanical properties of the catheter 18. If the distance withdrawn into catheter 18 is excessive there is a possibility that unexpected and unintentional impact of the used catheter 18 could result in bending of the catheter 18 over the sharp point 22 so increasing the possibility of the point puncturing the catheter wall and possibly causing injury. This possibility is greatly reduced by keeping the distance retracted inside the catheter 18 short.

The point 22 is used to cause the needle 20 to enter tissue and to provide a pathway for the catheter 18 to enter the tissue. When the chosen location is reached, for example in subcutaneous tissue or within the lumen of a vein, the needle 22 may be retracted by activating the catch member 30. Fluid such as parenteral medication or blood may be caused to pass through the needle 20 either before or after retraction to the position shown in FIG. 2. Preferably, the needle apparatus 10 is moved to the retracted position shown in FIG. 2 when it is still within the tissue and remains retracted when removed from the tissue after use so that the used and possibly contaminated sharp needle point 22 is never exposed. However, if retraction within the tissue is neglected or not preferred, retraction of the needle 20 can be effected after withdrawal from the tissue prior to disposal of the used needle apparatus 10.

When the needle 20 is withdrawn whilst still within the tissue the catheter 18 may be used to transport fluid into or out of the tissue. The withdrawal of the sharp needle point 22 from the tissue during use reduces the danger of damage to the tissue. For example if the needle is left in a vein the inner wall of the vein could be punctured.

Also, in the needle apparatus of the present invention the wall of the needle 20 is splintered and supported by the external elastic catheter 18. This allows the needle wall 20 to be thinner without kinking or breaking during use.

It is preferred that the catheter 18 is a close but sliding fit on the needle 20 and it is preferable that there is good resistance to fluid flow between the inner wall of the catheter 18 and the outer wall of the needle 20, so that for example when the needle 20 and the catheter 18 tips are located in a blood vessel, blood does not leak back into the housing 12 of the apparatus 10 as this may be undesirable in some circumstances. A constriction 36 or potential constriction of the catheter 18 may be provided if desired to achieve satisfactory sealing. The catheter 18 is also preferably tapered so as to have a very thin close fitting wall at its free end nearest needle point 22.

In FIGS. 3 and 4 there is shown a needle apparatus 40 which is similar to the needle apparatus 10 and like reference numerals denote like parts. In this case the catch member 30 includes a resilient part 32 of the wall of the housing 12 having a non-circular section shown in FIG. 4a such that compression of a long transverse axis or changed internal pressure causes the housing 12 to deform to form a circular section and in so doing release the flange 24 from restraint by engagement with the catch member 30. This allows the needle 20 to be retracted under urging of the spring 26 until the flange 24 engages with suitably placed projections 25 on the inner wall of the housing 12. These projections 25 act as a stop in a similar way to the guide means 28 shown in FIGS. 1 and 2 and result in the needle 20 moving from the exposed position shown in FIG. 3 to a protected position slightly inside the end of the catheter 18 as shown in FIG. 4.

In FIGS. 5 and 6 there is shown a needle apparatus 50 which is similar to the needle apparatus 10 and like reference numerals denote like parts. In this case, the catch member 30, shown in FIGS. 6a and 6b, is released by removing a slidable plate 52 so as to release the flange 24 from restraint and force the needle 20 to retract under urging from the spring 26. Further, once the plate 52 is removed it is difficult to re-extend the needle 20 to enter tissue a second time.

In FIGS. 7 and 8 there is shown a syringe 60 having a needle apparatus 10 as shown in FIGS. 1 and 2 mounted thereto. The syringe 60 includes a hollow cylindrical body 42 connected to the housing 12 such as by a Luer tapered fitting or a screw fitting or formed as one piece by injection molding. A plunger 44 is slidably mounted within the hollow body 42 in the conventional way. In this case, the catch member 30 may preferably be an elliptical and flexible portion of the housing 12 such that the pressure induced by depressing the plunger 44 may be sufficient to tend to cause the flexible portion of the housing 12 to become circular and release the catch member 30 automatically at the commencement of an injection. The retracted needle 20 would then be in a safe position for disposal before the injection is completed and before the needle apparatus is removed from its position within the tissue. Alternatively other catch means such as for example those described in FIGS. 1, 2, 5 and 6 which can be operated by finger pressure, may be fitted.

In FIGS. 9 and 10 there is shown a needle apparatus 70 which is similar to the needle apparatus 10 and like reference numerals denote like parts. In this case the functions of the guide means 28 and the spring 26 are combined in the form of a roll sock seal 72 which is sealingly attached peripherally to the inner wall of the housing 12 and centrally to the inner end of the needle 20. In the embodiment 70 illustrated tension of the roll sock seal 72 is biased such that it tends to retract the needle to the position shown in FIG. 10 when the catch member 30 is released by manual compression of the elliptical member 34 shown in FIG. 10a along its long axis.

In FIGS. 11, 12 and 13 there is shown a needle apparatus 80 which is similar to the needle apparatus 10 and like reference numerals denote like parts. In this case the catch member 30 incorporates a lever 92 which is pivotally mounted on a pivot 94 integrally formed with the housing 12. The lever 92 can be operated by finger pressure. The lever 92 has an angled extension 96 which engages with an aperture in the housing 12 in the condition shown in FIGS. 11 and 12. In this condition the flange 24 is retained against the spring 26 which is compressed. To release the flange 24 the lever 92 is pivoted about the pivot 94 so that the extension 96 is disengaged from the flange 24 which allows the spring 26 to expand and move the flange 24 into engagement with the guide means 28 as shown in FIG. 13. In this position the needle apparatus 10 would normally be used for fluid transfer in the tissue and would be ready for disposal after use. If desired the inner wall of the housing 12 may incorporate one or more wedge shaped ratchet projections (not shown) over which the flange 24 can ride in reaching a retracted position but which offer resistance to any attempt to push the needle into an extended position with the aim of improperly using it to enter tissue a second time.

In FIGS. 14, 15 and 16 there is shown a needle apparatus 120 which is similar to the needle apparatus 10 and like reference numerals denote like parts. In this case the housing 12 contains an L-shaped slot 122 in which is located a knob 124 attached to the flange 24. The knob 124 is initially located in a short lateral extension of the L-shaped slot 122 as shown in FIGS. 14 and 15. To release the spring 26, the knob 124 is moved as indicated by the arrow 126 into the longitudinal extension of the slot 122 which allows the spring 26 to expand to the position shown in FIG. 16, so retracting the needle 20. In an alternative arrangement the slot 122 has no lateral short extension and in this embodiment the spring 26 must be held in a compressed position as shown in FIG. 15 by continuous manual finger tip pressure exerted by the operator, so allowing the needle point 22 to penetrate the tissue. Release of the finger tip pressure would allow the spring 26 to return the flange 24 and the attached needle 20 to the position shown in FIG. 16 ready for fluid exchange to or from the tissue and subsequent safe disposal of the used needle apparatus 120.

In FIGS. 17, 18 and 19, there is shown a needle apparatus 150 which is similar to the needle apparatus 10 and like reference numerals denote like parts. In this case the needle 20 is connected to a rotatable body 152 which has a laterally extending drive pin 154. The drive pin 154 protrudes through an axially directed slot 156 in the housing 12 which may if desired incorporate a non-return catch. Outwardly, the drive pin 154 also engages a spiral slot or groove in a rotatable sleeve 158. Manual rotation of the sleeve 158 causes the pin 154 to move axially so causing extension or retraction of the needle 20 between the positions shown in FIGS. 18 and 19.

In FIGS. 20, 21 and 22 there is shown a needle apparatus 160 which is similar to the needle apparatus 10 and like reference numerals denote like parts. In this case the needle 20 has a second sharpened tip 168 at the end which passes through the guide means 28 within the housing 12. A piercable seal 166 is fixed to the inner wall of housing 12. In operation, when the needle point 22, in the extended position shown in FIG. 2, enters a blood vessel the puncture of the blood vessel is revealed to the operator by the appearance of blood in a sight chamber 176 between the guide member 28 and the seal 166. When the needle 20 is retracted, in this case by moving a knob 124 along a slot 122 in the direction of an arrow 126, the second needle point 168 is caused to pierce the seal 166. In this position a device such as a syringe or vacuum sampling tube fitted to the housing 12 through the opening 14 can be used to collect blood from a living body or transfer fluid into the blood vessel. The operator is protected from point 22 when it is in the retracted position shown in FIG. 22 and when the used needle apparatus 160 is removed from the living body.

In FIGS. 23, 24 and 25 there is shown a needle apparatus 170 which is similar to the needle apparatus 10 and similar to needle apparatus 160 and like reference numerals denote like parts. In this case the needle 20 has a side opening 174 at the end which passes through the guide means 28 within the housing 12. The inner, blunt, needle tip is closed and is located sealingly in an aperture in a guide means 172. In operation, when the needle point 22, in the extended position shown in FIG. 24, enters a blood vessel the puncture of the blood vessel is revealed to the operator by the appearance of blood in a sight chamber 176 located between the guide means 28 and the guide means 172. When the needle 20 is retracted, in this case by moving the knob 124 along the slot 122 in the direction of the arrow 126, the second needle aperture 174 passes into the open end of the housing 12. In this position a device such as a syringe or vacuum sampling tube fitted to the housing 12 through the opening 14 can be used to collect blood from the living body or transfer fluid into the blood vessel in which the point 22 is located. The operator is protected from the point 22 when it is in the retracted position shown in FIG. 25 and when the used needle apparatus 170 is removed from the living body.

In FIGS. 26, 27 and 28 there is shown a needle apparatus 180 which is similar to the needle apparatus 10 and like reference numerals denote like parts. In this case the catch member 30 is elongated so that the flange 28 is restrained in either the extended position shown in FIG. 26 or the retracted position shown in FIG. 27. The housing 12 is shaped at its outer end 14 to form a guide 184 adapted to receive the end bung 186 of a vacuum sampling vial 182. The guide 184 preferably has finger grips (not shown) formed upon its outer edge to assist an operator to hold it. A cup-shaped elastomer seal 188 attached to the inner wall of the guide 184, or, if preferred, the housing 12, closes the fluid pathway between the open end of the guide 184 and the needle tip 22. With the needle 20 in the retracted position shown in FIG. 27, the elastomer bung 186 of the vacuum sampling vial 182 pushes against the seal 188 and causes the second needle point 168 to first pierce the seal 188 and then pierce the elastomer bung 186. In this position fluid such as blood can flow between the vial 182 and the needle point 22. This arrangement allows the collection of blood from a vein which the needle point 22 has entered. When vacuum sampling vial 182 is removed from the needle apparatus 180, the elastomer seal 188, by virtue of its elasticity, returns to the position shown in FIG. 27, so sealing off the fluid path. A subsequent vacuum sampling vial 182 may then be pressed onto the seal 188 and a further blood collection made.

In FIGS. 29 and 30 there is shown a needle apparatus 220 which is similar to the needle apparatus 10 and to the needle apparatus 180 and like reference numerals denote like parts. In this case the housing 12 is shaped to form a guide 184 adapted to receive the end bung 186 of a vacuum sampling vial 182. An elastomer seal 224 is attached to the inner wall of the housing 12 and fitted over the inner end of the needle 20 which has a second sharpened end 168. The elastomer seal 224 is sealingly attached to the housing 12 or alternatively to a guide means 222 and fits closely about the inner end of needle 20 and is closed at one end so that the fluid path to and from needle 20 is closed. With the needle 20 in the extended position shown in FIG. 29 a small chamber 176 is formed near the second sharpened point 168 of the needle 20. If the needle point 22 is then caused to enter a blood vessel the operator may witness this as the appearance of blood in the small chamber 176. With the needle in the retracted position a vacuum sampling tube pressed onto the seal 224 will cause the second needle point 168 to puncture the seal 224 and then puncture the vacuum sampling tube bung 186, so allowing blood or other fluid to pass from the needle point 22 into the vacuum sampling vial 182. Removal of the vacuum sampling vial 182 allows the elastomer seal 224 to recover to the position shown in FIGS. 29 and 30, so sealing off the fluid path, ready for the fitting a subsequent vacuum sampling vial 182 and the collection of a further sample.

In FIGS. 31 and 32 there is shown a syringe 60 having a needle apparatus 240 mounted thereto. The needle apparatus 240 is similar to the needle apparatus 10 and like reference numerals denote like parts. In this case the flange 24 is elongated so as to engage the Luer tip 62 of a syringe which may be fitted to the needle apparatus 240 as shown in FIG.

32. The flange 24 and or the Luer tip 62 may be modified in shape to provide suitable engagement. The Luer tip 62 may be attached to a handle rather than a syringe. When the Luer tip 62 is entered into the mating housing 12 the flange 24 is advanced against the action of the spring 26 and the needle is extended ready to puncture tissue as required for an injection. Removal of the Luer tip 62 allows retraction of the the needle 20 as shown in FIG. 31. In this position a second device with, if desired, a modified Luer tip which does not engage the flange 24 may be fitted. Such a device may be connected, for example, to a tube able to deliver fluid for intravenous administration through the needle apparatus 240 in the retracted position shown in FIG. 31. A specially adapted flange and Luer tip are not shown, but they may each for example be semi-circular in section and arranged in a complementary way.

In FIGS. 33, 34 and 35 there is shown a tubular intravenous fluid line 254 having a needle apparatus 250 mounted thereto by means of guide means shaped to fit the intravenous line 254 and shown here as part 222. The Needle apparatus 250 is similar to needle apparatus 10 and like reference numerals denote like parts. In this case the housing 12 has formed upon it wing-shaped finger grips 252 to facilitate introduction of the pointed end 22 of the needle apparatus through the skin and through the wall of a blood vessel. When this is achieved, release of the catch member 30 as described hereinabove allows the needle 20 to retract and withdrawal of blood or administration of fluid intravenously can begin by connection of suitable receptacles to a Luer fitting 256. In this retracted position the device is also ready for safe disposal after use.

In FIGS. 36 and 38 there is shown a tubular intravenous fluid line 254 having a needle apparatus 270 mounted thereto by means of guide means shaped to fit the intravenous line 254 and shown here as part 222. The Needle apparatus 270 is similar to the needle apparatus 10 and to the needle apparatus 250 and like reference numerals denote like parts. In this case the housing 12 has formed upon it wing-shaped finger grips 252. Projections 272 are formed on each of the two wing-shaped finger grips 252 and when the finger grips are bent up in aposition as shown in FIG. 37 the projections 272 engage the flange 24 and prevent retraction of the needle 20 under the urging of the compressed spring 26. In this position the needle 20 is in the extended position and so may be used to enter a blood vessel. The wings 252 may if desired have formed upon them mating protrusions 274 and holes 276 such that when the wings 252 are bent up into apposition this position is locked or stabilised to facilitate use of the device to puncture the skin and enter a blood vessel. If preferred the projections 272 may be formed with suitable angles to interact with complementary angles on the flange 24 such that when the wings 252 are bent up into apposition the spring 26 is compressed and needle 20 is extended. Release of the wings to the position shown in FIG. 38 would make the device ready for administration of fluid intravenously and safe for subsequent disposal.

In FIGS. 39 and 40 of the drawings, there is shown a needle apparatus 340 including a Luer housing 12 or other suitable parenteral fluid connecting means having an open end 341 able to receive a mating Luer or similar fitting on a syringe or other injection device. A needle 20 has a sharpened free end 22 and is fixed through a closed end 342 of the housing 12. The housing 12 is mounted within an outer housing 343 having a closed end 344 narrowing down to a narrow forward portion 345.

A catheter 18 is fitted closely about the needle 20. The properties and dimensions of the catheter 18 are chosen so that the catheter 18 may slide axially and sealingly on the needle 20. If desired a constricted region 36 may be formed to assist sealing between the needle 20 and the catheter 18. The catheter 18 is fixed sealingly to the narrowed down portion 345 which is fitted concentrically around the needle 20. The outer housing 343 is adapted to fit about the outer wall of the housingm 12.

A catch member 30 having a substantially oval ring is fitted in slots 346 formed through part of the wall of the outer housing 343. The ring of the catch member 30 engages external ridges 13 on the housing 12 when the ring is in an oval configuration. However, the ring may be distorted to form a more nearly circular shape by finger pressure applied to the long axis of the oval. The arrangement is similar to that described hereinabove.

A coil or conical spring 26 is fitted between the closed ends 342 and 344. In a first position as shown in FIG. 39 the spring 26 is compressed. When the ring of the catch member 30 is distorted to allow it to pass the ridges 13 which act as a detent, the spring 26 causes the closed end 344 and the housing 343 to move forward to a second position shown in FIG. 2. The extent of travel is limited by a stop 17 located internally of the housing 15. It can be seen that in the second position the catheter 18 protrudes slightly beyond the sharp point 22 of the needle 20. It can also be seen that this movement has been effected without disturbing the attachment of the of the needle 20 to the housing 12 and without disturbing the fluid path through the housing 12 and the needle 20, fluid now being free to pass through part of the catheter 18.

In FIGS. 41, 42 an 43 of the drawings, there is shown a needle apparatus 350 which is similar to the needle apparatus 340 but differs principally in an alternative preferred arrangement in which the housing 12 is of narrower section at the closed end 342. The closed end 344 is adapted to fit around a narrower section 352 of the housing 12. In FIG. 43, a ring 354 is shown fitted in slots which are formed in part of the wall of the outer housing 343. The ring 354 is normally substantially oval or elliptical in shape. When in the substantially oval or, elliptical shape shown in FIG. 43 the ring 354 engages detente ridges 13 formed on an outer wall of the narrow section 352 of the housing 12. When distorted into a more circular form the ring 354 is able to pass the detente ridges 13 so that the outer housing 343 and closed end 344 are able to move from a first position as shown in FIG. 41 to a second position as shown in FIG. 42 under the urging of the spring 26.

In FIGS. 44, 45 and 46 of the drawings, there is shown a needle apparatus 360 which is similar to needle apparatus 340 but shows an alternative preferred arrangement of the needle housing 12 and a catheter base 362. In this embodiment the needle housing 12 has an extension, shown in the drawings as separate part 364, which encloses the spring 26 and is able to receive the catheter base 362. The needle housing 12 is further adapted by the fitting of a collar 368 which fits slidingly about the proximal end of the catheter 18 and acts as an end stop to limit movement of the catheter 18 to the second position shown in FIG. 45. In a first position, an oval ring 368, fitted through part of the walls of the housing 12 in the vicinity of parts 364 and 366, engages the catheter base 362. This is shown in schematic cross section in FIG. 46. When the ring 368 is distorted to a more circular form, the catheter base 362 is free to pass the ring 368 and under the urging of the spring 26 moves to a second position as shown in FIG. 45. During this movement the catheter 18 slides a short distance through the collar 366.

Figure 48:
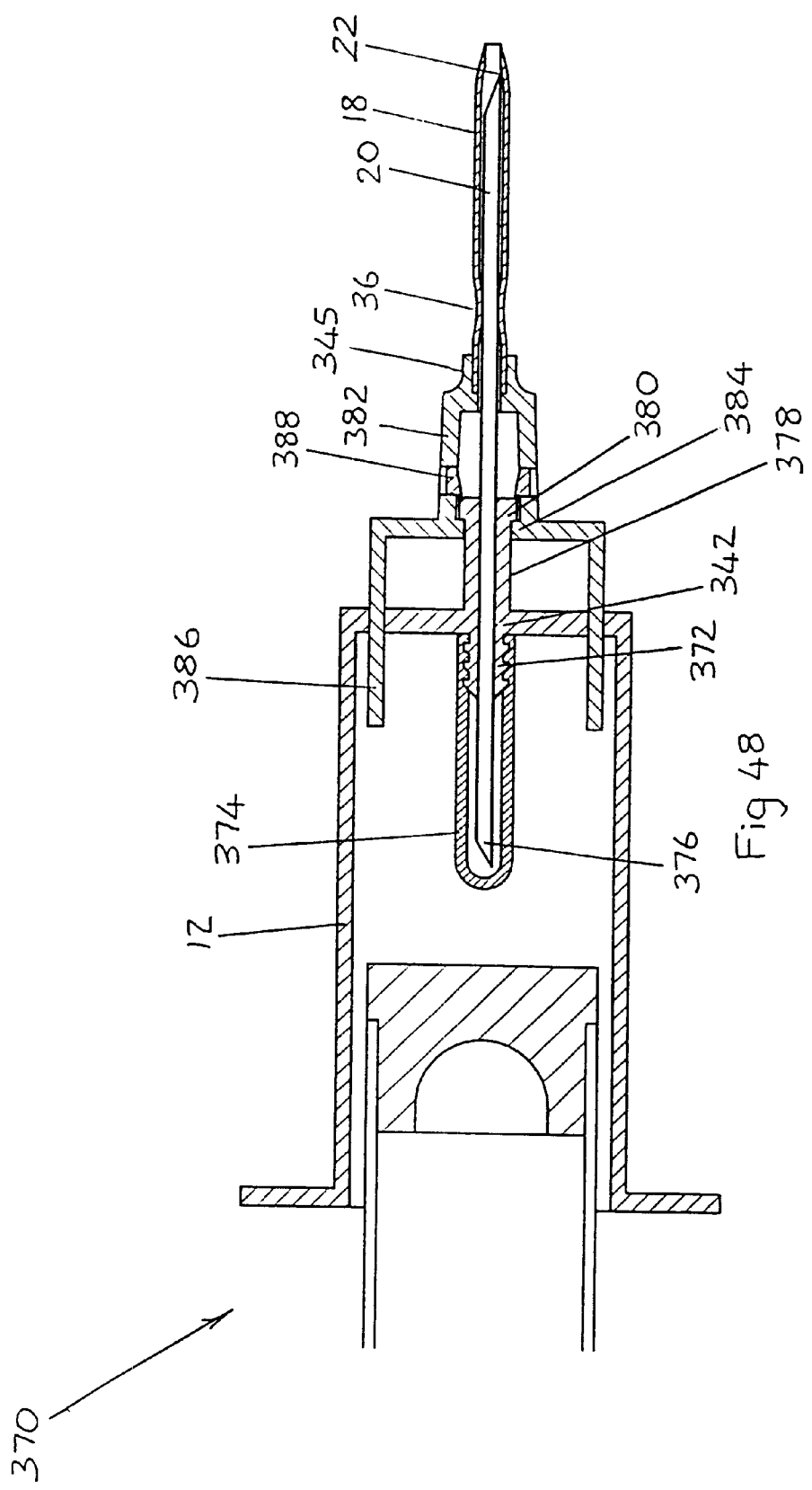
FIG. 48 is a view similar to FIG. 47 showing the needle apparatus after having been moved to a second position by the fitting of a vacuum sampling tube which is shown in part being removed ready to fit a subsequent vacuum sampling tube.

In FIGS. 47 and 48 of the drawings, there is shown a needle apparatus 370, the main feature of which is that it is adapted to accept vacuum sampling vial used in the collection of blood specimens. In this preferred embodiment the needle housing 12 is of substantially cylindrical form with an open end able to receive a standard vacuum sampling vial. The needle 20 is fixed through the closed end 342 of the housing 12. At the region where the needle 20 is attached therethrough, the closed end 342 has formed on an inner surface a boss 372, preferably formed with a ridged outer wall, able to receive an elastic elongated cap 374. The needle 20 has a sharpened inner end 376. The function of this arrangement is conventional. When the piercable bung of a vacuum sampling vial is pressed onto the cap 374 and advanced further, the inner needle point 376 first pierces the cap 374 then pierces the bung of the vacuum sampling vial, thereby opening a fluid transfer path into it. On the outer surface of the closed end 16 of housing 12 is a second boss 378 carrying on its outer end a flange 380 which is adapted to fit snugly within a catheter base 382. The catheter base 382, which is preferably of substantially cylindrical form, has a flange 384 formed upon it. The flange 384 has axial projections 386, which should preferably be, in sectional form, two arcs corresponding to two arcuate slots in the needle housing end 342. A hole in the flange 384 allows the axial movement of the outer needle housing boss 374 except at the projection 380 which is of larger diameter than the hole.

The needle apparatus 370 is shown in a first position in FIG. 47. When a vacuum sampling bung, such as that partly sketched in section in FIG. 48, is advanced into the housing 12, the bung is first pierced by inner needle point 376. When the vacuum sampling vial is advanced further by the operator it engages the inner ends of the projections 386 of the catheter base 382 so moving it axially. Thus, the angled inner surface of an elastic ring 388 rides over the projecting flange 380, so moving the catheter base 382 and catheter 18 from the first position shown in FIG. 47 to the second position as shown in FIG. 48, at which position further movement is prevented by the flange 380 engaging with the ring 388. The movement is made irreversible by the perpendicular surface of the proximal side of the ring 388. The form of this ring 388 is preferably substantially oval and generally similar to that shown in FIG. 46 but differs in having sloping walls which act as a non-return latch.

In the second position as shown in FIG. 48 a vacuum sampling vial which has been advanced over the needle point 376 of the needle 20 and which has collected blood from a vein through the tip of the catheter 18 and through the needle 20, can be removed without disturbing the relationship between parts 380, 384 and 388. During the removal of the vacuum sampling vial, the cap 374 recovers elastically to the position shown in the Figures, so sealing off any further flow of blood. The needle apparatus 370 is then ready to receive a subsequent vacuum sampling vial for the collection of further blood samples. This action does not disturb the relationship between the needle 20 and the catheter 18 because of the non-return construction of the elastic ring 388.

Figure 49:
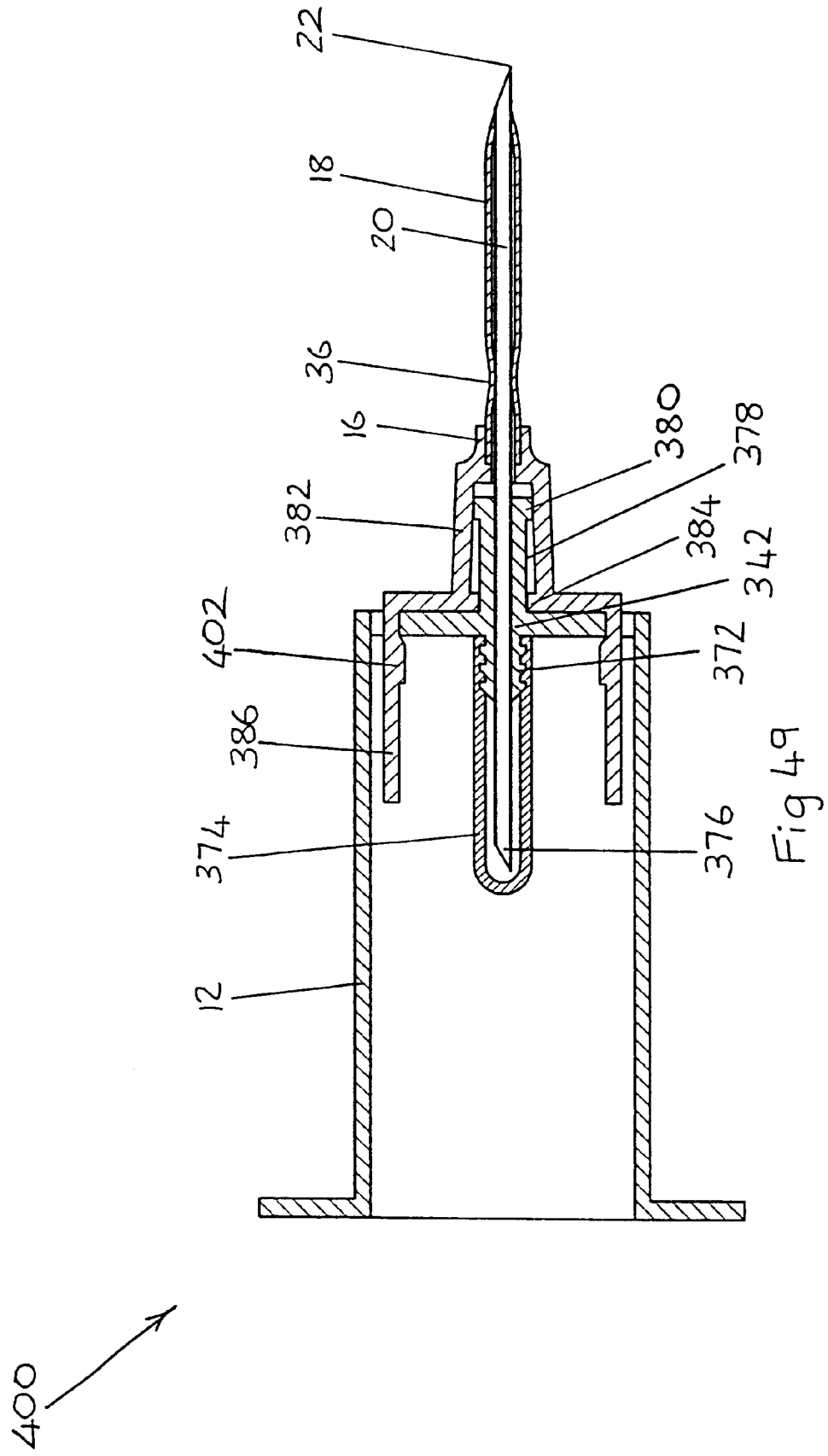
FIG. 49 is a longitudinal sectional view of a twentieth embodiment of the needle apparatus in accordance with the present invention shown in a first position ready to enter a blood vessel of a patient and ready to receive a vacuum sampling tube for the purpose of aspirating blood from the vein of a patient.
Figure 50:
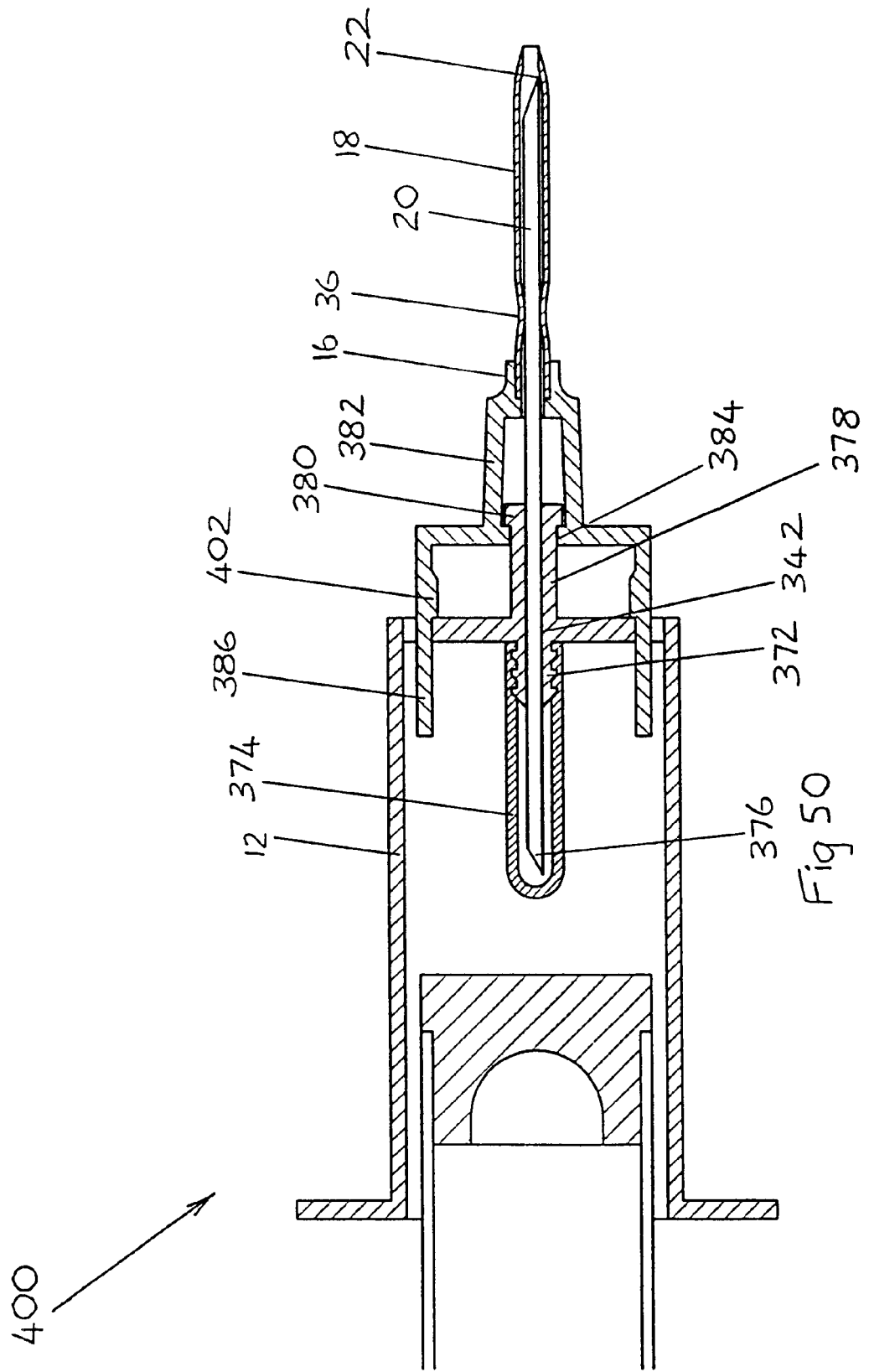
FIG. 50 is a view similar to FIG. 49 showing the needle apparatus after having been moved to a second position by the fitting of a vacuum sampling tube which is shown in part being removed ready to fit a subsequent vacuum sampling tube.

In FIGS. 49 and 50 of the drawings, there is shown a needle apparatus 400 which is generally similar in function to the needle apparatus shown in FIGS. 47 and 48 but has an alternative preferred arrangement for driving the catheter assembly from a first to a second position as a result of the advancement of a standard vacuum sampling tube. In this embodiment there is no elastic latching ring 388 and latching is achieved by the asymmetric form of ridges or detents 402 formed on the projections 386 on the catheter base 382. The projections 38 are preferably arcuate in section and fit snugly in matching arcuate slots in the end wall 342. The dimensions and elasticity of the materials are chosen such that the projections 386 pass freely through the slots in the end wall 342 of the housing 12 but moderate thumb pressure, applied through a vacuum sampling tube (part shown in FIG. 50) is required to cause the ridges 402 to pass through the slots.

FIG. 50 shows the needle apparatus 400 in a second position after pressure applied to the projections 386 has moved the catheter base 352 forward until stopped by flange 380 on the distal needle housing boss 378 engaging the edges of the hole in the flange 384, the hole having a smaller diameter than the flange 380. After collecting blood through the tip of the catheter 18 and the needle 20, the vacuum sampling vial maybe removed without disturbing the relationship between the parts of the needle apparatus 400 due to the non-return shape of the ridges 402 which resists movement back to the first position. Thus subsequent vacuum sampling vials maybe fitted and removed to collect a series of blood samples. At the completion of the procedure the needle apparatus 400 may be safely discarded because the needle point 22 is protected by the projecting catheter 18.

In FIGS. 51 to 54 there is shown a needle apparatus 500 in accordance with the present invention. In this embodiment, the needle 20 is provided with a flange 24.

Further, the needle 20 is held in its extended condition by means of an L-shaped stop member 502. The stop member 502 is attached internally of the housing 12 at a wall portion 504 which is relatively flexible.

When the housing 12 is subjected to decreased internal pressure the wall portion 504 moves inwardly as shown in FIG. 52 so that the stop member 502 moves laterally and releases the needle 20. Thus the needle 20 is able to retract so that the point 22 is within the catheter 18 as shown in FIG. 52.

Alternatively, when the housing 12 is subjected to increased internal pressure the wall portion 504 moves outwardly as shown in FIG. 54. Again the stop member 502 moves laterally and releases the needle 20 as shown in FIG. 54 so that the needle 20 is retracted.

It should be appreciated that the scope of the present invention need not be limited to the particular scope of the embodiments described above.

What is claimed is:

1. A needle apparatus comprising a thin walled catheter having a free end closely enclosing a tubular needle having a sharp point, characterised in that the needle and/or the catheter is mounted to a housing and the needle and the catheter are longitudinally moveable relative to one another between a first position at which the needle extends from the catheter a short distance and a second position at which the sharp point is located within the catheter adjacent the free end thereof, the needle remaining in a fluid pathway of the needle apparatus at all times, first means for positively retaining the needle and the catheter in the first position, the first means includes a manually operable catch member which upon actuation by a user releases the needle and the catheter to move relatively to the second position, second means for moving the needle relative to the catheter to the second position upon release of the catch member, and the needle apparatus being arranged to pierce tissue when the catheter and the needle are in the first position.

2. A needle apparatus according to claim 1, characterised in that the second means for moving the needle relative to the catheter to the second position is automatically operable upon release of the catch member.

3. A needle apparatus according to claim 2, characterised in that spring means is provided to move the needle to the second position.

4. A needle apparatus according to claim 3, characterised in that the spring means is a coil spring mounted about the needle.

5. A needle apparatus according to claim 1, characterised in that the housing is provided with means for attachment to a syringe or a fluid collection vial.

6. A needle apparatus according to claim 1, characterised in that a flange is mounted on the needle and the catch member engages with the flange in the first position of the needle and the catheter.

7. A needle apparatus according to claim 6, characterised in that the flange is substantially circular and the catch member includes a deformable member which is in the form of an elliptical ring which can be deformed to a substantially circular shape to enable the flange to pass through the catch member.

8. A needle apparatus according to claim 7, characterised in that the elliptical ring is integrally formed with a wall portion of the housing.

9. A needle apparatus according to claim 1, characterised in that the relative movement of the needle and the catheter to the second position is positively restricted.

10. A needle apparatus according to claim 1, characterised in that the needle and the catheter are positively retained in the second position.

11. A needle apparatus according to claim 1, characterised in that the needle has a rearward end containing an aperture, such that upon movement of the needle to the second position the aperture at the rearward end of the needle establishes communication with a chamber which contains or is arranged to contain fluid.

12. A needle apparatus according to claim 11, characterised in that the rearward end of the needle has a further sharp point arranged to pierce a barrier member in the housing when the needle moves to the second position.

13. A needle apparatus according to claim 12, characterised in that the needle moves relative to the housing when the needle and the catheter move relatively from the first position to the second position whilst the catheter remains stationary relative to the housing, the housing is arranged to receive a container containing or arranged to contain fluid, a seal is mounted about the rearward end of the needle so that the fluid pathway to and from the needle is closed, the seal remaining intact when the needle moves to the second position, the seal being punctured by the further sharp point with the needle in the second position as the container is engaged with the housing, and the further sharp point then punctures a wall of the container to open the fluid pathway between the needle and the container.

14. A needle apparatus according to claim 1, characterised in that the needle moves relative to the housing when the needle and the catheter move relatively from the first position to the second position whilst the catheter is stationary relative to the housing.

15. A needle apparatus according to claim 14, characterised in that the first means further provides for irreversibly preventing the needle from moving back towards the first position once the needle and the catheter have reached the second position.

16. A needle apparatus according to claim 1, characterised in that the catheter moves relative to the housing when the needle and the catheter move relatively from the first position to the second position whilst the needle is stationary relative to the housing.

17. A needle apparatus according to claim 16, characterised in that the housing is arranged to receive a chamber which contains or is arranged to contain fluid, and that the catheter mounting is such that as the chamber is received by the housing the catheter is caused to be moved over the sharp point of the needle.

18. A needle apparatus according to claim 16, characterised in that the first means provides for irreversibly preventing the catheter from moving back towards the first position once the needle and the catheter have reached the second position.

19. A needle apparatus according to claim 1, characterised in that the needle defines a part of this fluid pathway which is of substantially constant bore throughout the length of the needle.

20. A needle apparatus comprising a thin walled catheter having a free end closely enclosing a tubular needle having a sharp point, characterised in that the needle and the catheter are longitudinally moveable relative to one another between a first position at which the needle extends from the catheter a short distance and a second position at which the sharp point is located within the catheter adjacent the free end thereof, the needle remaining in the fluid pathway of the needle apparatus at all times, means being provided for positively retaining the needle and the catheter in the first position including a catch member which upon release enables the needle and the catheter to move to the second position, the needle apparatus being arranged to pierce tissue when the catheter and the needle are in the first position, wherein the needle has a rearward end containing an aperture and having a further sharp point arranged to pierce a barrier member in the housing when the catheter and the needle move to the second position so as to establish fluid communication with a chamber which contains or is arranged to contain fluid.

21. A needle apparatus comprising a thin walled catheter having a free end closely enclosing a tubular needle having a sharp point, characterised in that the needle and the catheter are longitudinally moveable relative to one another between a first position at which the needle extends from the catheter a short distance and a second position at which the sharp point is located within the catheter adjacent the free end thereof, the needle remaining in fluid pathway of the needle apparatus at all times, means being provided for positively retaining the needle and the catheter in the first position including a catch member which upon release enables the needle and the catheter to move to the second position, the needle apparatus being arranged to pierce tissue when the catheter and the needle are in the first position, means being provided for positively retaining the needle and the catheter in the first position wherein the apparatus includes a housing having a flexible wall portion which upon a change in internal pressure of the housing moves laterally to act as the catch member to enable the catheter and the needle to move to the second position.

* * * * *